US008956274B2

(12) United States Patent
Schneider et al.

(10) Patent No.: US 8,956,274 B2
(45) Date of Patent: Feb. 17, 2015

(54) TRANSCRANIAL MAGNETIC STIMULATION FIELD SHAPING

(75) Inventors: M. Bret Schneider, Portola Valley, CA (US); David J. Mishelevich, Playa del Rey, CA (US)

(73) Assignee: Cervel Neurotech, Inc., Redwood City, CA (US)

( * ) Notice: Subject to any disclaimer, the term of this patent is extended or adjusted under 35 U.S.C. 154(b) by 867 days.

(21) Appl. No.: 12/838,299

(22) Filed: Jul. 16, 2010

(65) Prior Publication Data

US 2010/0286470 A1    Nov. 11, 2010

Related U.S. Application Data

(63) Continuation-in-part of application No. 12/670,938, filed as application No. PCT/US2008/073751 on Aug. 20, 2008, application No. 12/838,299, which is a continuation-in-part of application No. 12/701,395, (Continued)

(51) Int. Cl.
*A61N 2/00* (2006.01)
*A61N 2/02* (2006.01)

(52) U.S. Cl.
CPC .. *A61N 2/006* (2013.01); *A61N 2/02* (2013.01)
USPC ............................................. 600/14

(58) Field of Classification Search
USPC ....................... 600/9–15, 407, 424
See application file for complete search history.

(56) References Cited

U.S. PATENT DOCUMENTS

| 3,799,164 A | 3/1974 | Rollins |
| 4,134,395 A | 1/1979 | Davis |
| 4,889,526 A | 12/1989 | Rauscher et al. |
| 5,207,223 A | 5/1993 | Adler |

(Continued)

FOREIGN PATENT DOCUMENTS

| DE | 10242542 A1 | 4/2004 |
| EP | 0501048 A1 | 9/1992 |

(Continued)

OTHER PUBLICATIONS

Bodo et al.; The role of multidrug transporters in drug availability, metabolism and toxicity; Toxicol Lett; pp. 140-141; Review; pp. 133-143; Apr. 11, 2003.

(Continued)

*Primary Examiner* — Christine Matthews
(74) *Attorney, Agent, or Firm* — Shay Glenn LLP

(57) ABSTRACT

Described herein are Transcranial Magnetic Simulation (TMS) systems and methods of using them for emitting focused, or shaped, magnetic fields for TMS. In particular, described herein are arrays of TMS electromagnets comprising at least one primary (e.g., central) TMS electromagnet and a plurality of secondary (e.g., lateral or surrounding) TMS electromagnets. The secondary TMS electromagnets are arranged around the primary TMS electromagnet(s), and are typically configured to be synchronously fired with the primary TMS electromagnets. Secondary TMS electromagnets may be fired at a fraction of the power used to energize the primary TMS electromagnet to shape the resulting magnetic field. The secondary TMS electromagnets may be stimulated at opposite polarity to the primary TMS electromagnet(s). Focusing in this manner may prevent or reduce stimulation of adjacent non-target brain regions.

21 Claims, 13 Drawing Sheets

Related U.S. Application Data filed on Feb. 5, 2010, which is a continuation-in-part of application No. PCT/US2008/075575, filed on Sep. 8, 2008, application No. 12/838,299, which is a continuation-in-part of application No. 12/185,544, filed on Aug. 4, 2008, now abandoned, application No. 12/838,299, which is a continuation-in-part of application No. 12/324,227, filed on Nov. 26, 2008, now Pat. No. 8,267,850.

(60) Provisional application No. 60/956,920, filed on Aug. 20, 2007, provisional application No. 60/970,958, filed on Sep. 9, 2007, provisional application No. 61/077,488, filed on Jul. 2, 2008, provisional application No. 60/970,534, filed on Sep. 7, 2007, provisional application No. 60/970,532, filed on Sep. 7, 2007, provisional application No. 60/975,177, filed on Sep. 26, 2007, provisional application No. 60/954,018, filed on Aug. 5, 2007, provisional application No. 60/990,300, filed on Nov. 27, 2007, provisional application No. 60/992,385, filed on Dec. 5, 2007, provisional application No. 61/227,000, filed on Jul. 20, 2009.

(56) References Cited

U.S. PATENT DOCUMENTS

| | | | |
|---|---|---|---|
| 5,267,938 | A | 12/1993 | Konotchick |
| 5,427,097 | A | 6/1995 | Depp |
| 5,441,495 | A | 8/1995 | Liboff et al. |
| 5,531,227 | A | 7/1996 | Schneider |
| 5,707,334 | A | 1/1998 | Young |
| 5,738,625 | A | 4/1998 | Gluck |
| 5,766,124 | A | 6/1998 | Polson |
| 5,891,034 | A | 4/1999 | Bucholz |
| 6,042,531 | A | 3/2000 | Holcomb |
| 6,132,361 | A | 10/2000 | Epstein et al. |
| 6,132,631 | A | 10/2000 | Nallan et al. |
| 6,149,577 | A | 11/2000 | Bouldin et al. |
| 6,179,770 | B1 | 1/2001 | Mould |
| 6,179,771 | B1 | 1/2001 | Mueller |
| 6,198,958 | B1 | 3/2001 | Ives et al. |
| 6,236,875 | B1 | 5/2001 | Bucholz et al. |
| 6,266,556 | B1 | 7/2001 | Ives et al. |
| 6,351,573 | B1 | 2/2002 | Schneider |
| 6,356,781 | B1 | 3/2002 | Lee et al. |
| 6,425,852 | B1 | 7/2002 | Epstein et al. |
| 6,447,440 | B1 | 9/2002 | Markoll |
| 6,461,289 | B1 | 10/2002 | Muntermann |
| 6,488,617 | B1 | 12/2002 | Katz |
| 6,507,751 | B2 | 1/2003 | Blume et al. |
| 6,537,197 | B1 | 3/2003 | Ruohonen et al. |
| 6,571,123 | B2 | 5/2003 | Ives et al. |
| 6,572,528 | B2 | 6/2003 | Rohan et al. |
| 6,663,556 | B2 | 12/2003 | Barker |
| 6,818,669 | B2 | 11/2004 | Moskowitz et al. |
| 6,849,040 | B2 | 2/2005 | Ruohonen et al. |
| 6,858,000 | B1 | 2/2005 | Schukin et al. |
| 6,972,097 | B2 | 12/2005 | Yoshida et al. |
| 7,023,311 | B2 | 4/2006 | Baldwin et al. |
| 7,087,008 | B2 | 8/2006 | Fox et al. |
| 7,088,210 | B2 | 8/2006 | Day et al. |
| 7,104,947 | B2 | 9/2006 | Riehl |
| 7,141,028 | B2 | 11/2006 | McNew |
| 7,153,256 | B2 | 12/2006 | Riehl et al. |
| 7,155,284 | B1 | 12/2006 | Whitehurst et al. |
| 7,236,830 | B2 | 6/2007 | Gliner |
| 7,239,910 | B2 | 7/2007 | Tanner |
| 7,367,935 | B2 | 5/2008 | Mechlenburg et al. |
| 7,367,936 | B2 | 5/2008 | Myers et al. |
| 7,396,326 | B2 | 7/2008 | Ghiron et al. |
| 7,437,196 | B2 | 10/2008 | Wyler et al. |
| 7,483,747 | B2 | 1/2009 | Gliner et al. |
| 7,520,848 | B2 | 4/2009 | Schneider et al. |
| 7,771,341 | B2 | 8/2010 | Rogers |
| 7,856,264 | B2 | 12/2010 | Firlik et al. |
| 7,904,134 | B2 | 3/2011 | McIntyre et al. |
| 2002/0022777 | A1 * | 2/2002 | Crieghton et al. ............ 600/407 |
| 2002/0042563 | A1 | 4/2002 | Becerra et al. |
| 2002/0097125 | A1 | 7/2002 | Davey |
| 2003/0004392 | A1 | 1/2003 | Tanner et al. |
| 2003/0028072 | A1 | 2/2003 | Fischell et al. |
| 2003/0065243 | A1 | 4/2003 | Tanner |
| 2003/0204135 | A1 | 10/2003 | Bystritsky |
| 2004/0010177 | A1 | 1/2004 | Rohan et al. |
| 2004/0077921 | A1 | 4/2004 | Becker et al. |
| 2004/0078056 | A1 | 4/2004 | Zangen et al. |
| 2004/0193000 | A1 | 9/2004 | Riehl |
| 2004/0193002 | A1 | 9/2004 | Tanner et al. |
| 2005/0033154 | A1 | 2/2005 | deCharms |
| 2005/0038313 | A1 | 2/2005 | Ardizzone |
| 2005/0046532 | A1 | 3/2005 | Dodd |
| 2005/0107655 | A1 | 5/2005 | Holzner |
| 2005/0113630 | A1 | 5/2005 | Fox et al. |
| 2005/0124848 | A1 | 6/2005 | Holzner |
| 2005/0148808 | A1 | 7/2005 | Cameron et al. |
| 2005/0154426 | A1 | 7/2005 | Boveja et al. |
| 2005/0222625 | A1 | 10/2005 | Laniado et al. |
| 2005/0234286 | A1 | 10/2005 | Riehl et al. |
| 2005/0256539 | A1 | 11/2005 | George et al. |
| 2006/0058853 | A1 | 3/2006 | Bentwich |
| 2006/0094924 | A1 | 5/2006 | Riehl et al. |
| 2006/0106430 | A1 | 5/2006 | Fowler et al. |
| 2006/0122454 | A1 | 6/2006 | Riehl et al. |
| 2006/0122496 | A1 | 6/2006 | George et al. |
| 2006/0149337 | A1 | 7/2006 | John |
| 2006/0173274 | A1 | 8/2006 | George et al. |
| 2006/0189866 | A1 | 8/2006 | Thomas et al. |
| 2006/0199992 | A1 | 9/2006 | Eisenberg et al. |
| 2006/0218790 | A1 | 10/2006 | Day et al. |
| 2006/0287566 | A1 | 12/2006 | Zangen et al. |
| 2007/0027353 | A1 | 2/2007 | Ghiron et al. |
| 2007/0027504 | A1 | 2/2007 | Barrett et al. |
| 2007/0083074 | A1 | 4/2007 | Sotiriou |
| 2007/0100392 | A1 | 5/2007 | Maschino et al. |
| 2007/0100398 | A1 | 5/2007 | Sloan |
| 2007/0242406 | A1 | 10/2007 | Annis et al. |
| 2007/0260107 | A1 | 11/2007 | Mishelevich |
| 2007/0265489 | A1 | 11/2007 | Fowler et al. |
| 2007/0293916 | A1 | 12/2007 | Peterchev |
| 2008/0033297 | A1 | 2/2008 | Sliwa |
| 2008/0058582 | A1 | 3/2008 | Aho et al. |
| 2008/0064950 | A1 | 3/2008 | Ruohonen et al. |
| 2008/0123922 | A1 | 5/2008 | Gielen et al. |
| 2008/0161636 | A1 | 7/2008 | Hurme et al. |
| 2008/0306326 | A1 | 12/2008 | Epstein |
| 2009/0018384 | A1 | 1/2009 | Boyden et al. |
| 2009/0024021 | A1 | 1/2009 | George et al. |
| 2009/0099405 | A1 | 4/2009 | Schneider et al. |
| 2009/0099623 | A1 | 4/2009 | Bentwich |
| 2009/0112133 | A1 | 4/2009 | Deisseroth et al. |
| 2009/0112277 | A1 | 4/2009 | Wingeier et al. |
| 2009/0114849 | A1 | 5/2009 | Schneider et al. |
| 2009/0124848 | A1 | 5/2009 | Miazga |
| 2009/0156884 | A1 | 6/2009 | Schneider et al. |
| 2009/0187062 | A1 | 7/2009 | Saitoh |
| 2009/0189470 | A1 | 7/2009 | McClellan |
| 2009/0227830 | A1 | 9/2009 | Pillutla et al. |
| 2009/0234243 | A1 | 9/2009 | Schneider et al. |
| 2010/0004500 | A1 | 1/2010 | Gliner et al. |
| 2010/0185042 | A1 | 7/2010 | Schneider et al. |
| 2010/0210894 | A1 | 8/2010 | Pascual-Leone et al. |
| 2011/0184223 | A1 | 7/2011 | Peterchev et al. |
| 2011/0273251 | A1 | 11/2011 | Mishelevich et al. |
| 2012/0016177 | A1 | 1/2012 | Mishelevich et al. |
| 2013/0096363 | A1 | 4/2013 | Schneider et al. |
| 2013/0317281 | A1 | 11/2013 | Schneider et al. |

FOREIGN PATENT DOCUMENTS

| | | |
|---|---|---|
| EP | 0709115 A1 | 5/1996 |
| EP | 0788813 A1 | 8/1997 |

(56) References Cited

FOREIGN PATENT DOCUMENTS

| | | |
|---|---|---|
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |
| WO | WO 2006/124914 A2 | 11/2006 |
| WO | WO 2007/050592 A2 | 5/2007 |
| WO | WO 2007/130308 A2 | 11/2007 |
| WO | WO 2009/042863 A1 | 4/2009 |

OTHER PUBLICATIONS

Wasan et al.; Lipid transfer protein I facilitated transfer of cyclosporine from low-to high-density lipoproteins is only partially dependent on its cholesteryl ester transfer activity; J Pharmacol Exp Ther; 284(2); pp. 599-605; Feb. 1998.

Schneider et al.; U.S. Appl. No. 13/808,806 entitled "Transcranial magnetic stimulation for altering susceptibility of tissue to pharmaceuticals and radiation," filed Apr. 23, 2013.

Dantec magnetic stimulation product information on MagPro X100 with MagOption; http://www.danica.nl/neuro/neuro-magnetische-stimulatoren.htm; Jan. 15, 2009.

Hayward et al.; The role of the anterior cingulate cortex in the counting stroop task; Exp Brain Res; vol. 154(3); pp. 355-358; Feb. 2004.

Hsu et al., Analysis of Efficiency of Magnetic Stimulation; IEEE Transactions on Biomedical Engineering; vol. 50. No. 11; Sep. 2003; pp. 1276-1285.

Kamitani et al.; A model of magnetic stimulation of neocortical neurons; Neurocomputing; vol. 38; No. 40; Jun. 2001; pp. 697-703.

Kandel et al.; Chapter 12: Synaptic Integration; Principles of Neural Science; Editors: Kandel, Schwartz and Jessell; 4th Edition, McGraw-Hill; pp. 208-227; Jan. 5, 2000.

Lefaucheur, Jean-Pascal; Use of repetitive transcranial magnetic stimulation in pain relief; Expert Rev Neurother; vol. 8, No. 5: pp. 799-808; May 2008.

Lefaucheur et al.; Pain relief induced by repetitive transcranial magnetic stimulation of precentral cortex; Neuroreport; vol. 12, issue 13: pp. 2963-2965; Sep. 17, 2001.

Lefaucheur et al.; Somatotopic organization of the analgesic effects of motor cortex rTMS in neuropathic pain; Neurology; vol. 67, No. 11: pp. 1998-2004; Dec. 12, 2006.

Levkovitz et al.; A randomized controlled feasibility and safety study of deep transcranial magnetic stimulation; Clin. Neurophysiol.; vol. 118(12); pp. 2730-2744; Dec. 2007.

Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.

Rossini et al.; Transcranial magnetic stimulation: Diagnostic, therapeutic, and researchpotential; Neurology; vol. 68, No. 7: pp. 484-488; Feb. 13, 2007.

Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.

Wagner et al.; Transcranial direct current stimulation: A computer-based human model study; NeuroImage; vol. 35; issue 3; Apr. 15, 2007; pp. 1113-1124.

Yang et al.; 3D Realistic Head Model Simulation Based on Transcranial Magnetic Stimulation; Conf Proc IEEE Eng Med Biol Soc.; vol. Suppl.; Aug. 30-Sep. 3, 2006; 4 pages.

Yu et al.; Pathogenesis of normal-appearing white matter damage in neuromyelitis optica: diffusion-tensor MR imaging; Radiology; vol. 246, No. 1: pp. 222-228; Jan. 2008.

Schneider, M. Bret .; U.S. Appl. No. 13/169,967 entitled "Enhanced Spatial Summation for Deep-Brain Transcranial Magnetic Stimulation," filed Jun. 27, 2011.

Sadler, John W.; U.S. Appl. No. 13/512,496 entitled "Power Management in Transcranial Magnetic Stimulators," filed Sep. 17, 2012.

Schneider et al.; U.S. Appl. No. 13/586,640 entitled "Transcranial Magnet Stimulation of Deep Brain Targets," filed Aug. 15, 2012.

Partsch et al.; U.S. Appl. No. 12/669,882 entitled "Device and method for treating hypertension via non-invasive neuromodulation," filed Jun. 2, 2010.

Schneider et al.; U.S. Appl. No. 12/671,260 entitled "Gantry and switches for position-based triggering of tms pulses in moving coils," filed Jun. 17, 2010.

Mishelevich et al.; U.S. Appl. No. 12/670,938 entitled "Firing patterns for deep brain transcranial magnetic stimulation," filed Jun. 17, 2010.

Mishelevich et al.; U.S. Appl. No. 12/677,220 entitled "Focused magnetic fields," filed Mar. 9, 2010.

Mishelevich et al.; U.S. Appl. No. 12/679,960 entitled "Display of modeled magnetic fields," filed Mar. 25, 2010.

Mishelevich et al.; U.S. Appl. No. 12/680,749 entitled "Intra-session control of transcranial magnetic stimulation," filed Mar. 30, 2010.

Mishelevich et al.; U.S. Appl. No. 12/680,912 "Transcranial magnetic stimulation with protection of magnet-adjacent structures," filed Mar. 31, 2010.

Agnew et al.; Considerations for safety in the use of extracranial stimulation for motor evoked potentials; Neurosurgery; vol. 20; pp. 143-147; 1987.

Avery et al.; A Controlled Study of Repetitive Transcranial Magnetic Stimulation in Medication-Resistant Major Depression; Biological Psychiatry; vol. 59; pp. 187-194; 2005.

Barker et al.; Non invasive magnetic stimulation of the human motor cortex; Lancet; vol. 1; pp. 1106-1110; 1985.

Barker, A. T.; An introduction to the basic principles of magnetic nerve stimulation; Journal of Clinical Neurophysiology; vol. 8; No. 1; pp. 26-37; 1991.

Basser et al.; Stimulation of myelinated nerve axon by electromagnetic induction; Medical & Biological Engineering and Computing.; vol. 29; pp. 261-268; 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; 2002.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; 2004.

Davey et al.; Prediction of magnetically induced electric fields in biologic tissue; IEEE Transactions on Biomedical Engineering; vol. 38; pp. 418-422; 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

(56) References Cited

OTHER PUBLICATIONS

George, Mark S.; Stimulating the brain; Scientific American; Sep. 2002; pp. 67-73.
Han et al.; Multichannel magnetic stimulation system design considering mutual couplings among the stimulation coils; IEEE Trans. on Biomedical Engineering; vol. 51; No. 5; pp. 812-817; May 2004.
Hemond et al.; Transcranial magnetic stimulation in neurology: What we have learned from randomized controlled studies; Neuromodulation: Technology at the Neural Interface; vol. 10; No. 4; pp. 333-344; 2007.
Hovey, C. et al.; The new guide to magnetic stimulation; The Magstim Company Ltd.; Carmarthenshire, United Kingdom; 2003.
Huang et al.; Theta Burst Stimulation of the Human Motor Cortex; Neuron; vol. 45; pp. 201-206; 2005.
Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.
Lang et al.; How does transcranial DC stimulation of the primary motor cortex alter regional neuronal activity in the human brain?; Eur. J. Neurosci.; vol. 22; No. 2; pp. 495-504; Jul. 2005.
Lin et al.; Magnetic coil design considerations for functional magnetic stimulation; IEEE Trans. on Biomedical Eng.; vol. 47; No. 5; pp. 600-610; May 2000.
Magstim Website: http://www.magstim.com/magneticstimulators/magstimacc/12494.html (printed Mar. 23, 2010).
Martin et al.; Transcranial magnetic stimulation for treating depression; Cochrane Review; 2002 (In (eds.): The Cochrane Library. Oxford: Update Software: The Cochrane Library. Oxford: Update Software.).
Mayberg et al.; Deep brain stimulation for treatment-resistant depression; Neuron; vol. 45; pp. 651-660; 2005.
Nadeem et al.; Computation of electric and magnetic stimulation in human head using the 3-D impedance method; IEEE Trans on Biomedical Eng; vol. 50; No. 7; pp. 900-907; Jul. 2003.
Ohnishi et al.; rCBF changes elicited by rTMS over DLPFC in humans; Suppl Clin Neurophysiol.; vol. 57: pp. 715-720; 2004.
Paton et al.; Vascular-brain signaling in hypertension: role of angiotensin II and nitric oxide; Curr. Hypertens Rep; vol. 9; No. 3; pp. 242-247; Jun. 2007.
Roth et al.; A coil design for transcranial magnetic stimulation of adeep brain regions; J. Clin. Neurophysiology; vol. 19; No. 4; 2002; pp. 361-370.
Ruohonen et al.; Theory of Multichannel Magnetic Stimulation: Toward Functional Neuromuscular Rehabilitation; IEEE Transactions on Biomedical Engineering; vol. 46; No. 6; pp. 646-651; Jun. 1999.
Ruohonen, J.; Transcranial magnetic stimulation: modelling and new techniques; (doctoral dissertation); Helsinki Univ. of Tech.; Dept. of Eng. Physics and Mathematics; Espoo, Finland; 1998.
Ruohonen et al.; (Chapter 2); Magnetic stimulation in clinical neurophysiology; Second Ed.; Ed. Elsevier Inc.; pp. 17-30; 2005.
Ruohonen et al.; Focusing and targeting of magnetic brain stimulation using multiple coils; Medical & Biological Engineering and Computing; vol. 35; pp. 297-301; 1998.
Sackheim, H. A.; Commentary: Magnetic stimulation therapy and ECT; Convulsive Therapy; vol. 10; No. 4; 1994; pp. 255-285.
Sekino et al.; Comparison of current distributions in electroconvulsive therapy and transcranial magnetic stimulation; J. of Applied Physics; vol. 91; No. 10; pp. 8730-8732; May 15, 2002.
Speer et al.; Opposite effects of high and low frequency rTMS on regional brain activity in depressed patients; Biol. Psychiatry; vol. 48; No. 12; pp. 1133-1141; Dec. 15, 2000.
Takano et al.; Short-term modulation of regional excitability and blood flow in human motor cortex following rapid-rate transcranial magnetic stimulation; Neuroimage; vol. 23; No. 3; pp. 849-859; Nov. 2004.
Traad, Monique; A Quantitative Positioning Device for Transcranial Magnetic Stimulation; Engineering in Medicine and Biology Society; 1990; Proceedings of the 12th Annual Int'l Conf. of the IEEE; Philadelphia, PA; p. 2246; Nov. 1-4, 1990.
Ueno et al.; Localized stimulation of neural tissues in the brain by means of a paired configuration of time-varying magnetic fields; J. Appl. Phys.; vol. 64; No. 10; pp. 5862-5864; Nov. 15, 1988.
Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.
Wagner et al.; Three-dimensional head model simulation of transcranial magnetic stimulation; IEEE Trans. on Biomedical Engineering; vol. 51; No. 9; pp. 1586-1598; Sep. 2004.
Waki et al.; Junctional adhesion molecule-1 is upregulated in spontaneously hypertensive rats: evidence for a prohypertensive role within the brain stem; Hypertension; vol. 49; No. 6; pp. 1321-1327; Jun. 2007.
Wasserman et al.; Therapeutic application of repetitive magnetic stimulation: a review; Clinical Neurophysiology; vol. 112; pp. 1367-1377; 2001.
Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; 1998.
Xiao et al.; Magnetic Nanocomposite Paste: An Ideal High-$\mu$, k and Q Nanomaterial for Embedded Inductors in High Frequency Electronic Appls.; Proceedings of the 9th World Multiconference on Systemics, Cybernetics and Informatics; Orlando, FL; Jul. 10-13, 2005.
Aleman et al.; Efficacy of slow repetitive transcranial magnetic stimulation in the treatment of resistant auditory hallucinations in schizophrenia: a meta-analysis; J Clin Psychiatry; 68(3):416-21; Mar. 2007.
Alonso et al.; Right prefrontal repetitive transcranial magnetic stimulation in obsessive-compulsive disorder: a double-blind, placebo-controlled study; Am J Psychiatry; 158(7):1143-5; Jul. 2001.
Antal et al.; Transcranial Direct Current Stimulation Over Somatosensory Cortex Decreases Experimentally Induced Acute Pain Perception; Clin J Pain; vol. 24, No. 1; pp. 56-63; Jan. 2008.
Bikson et al.; Transcranial Direct Current Stimulation for Major Depression: A General System for Quantifying Transcranial Electrotherapy Dosage; Current Treatment Options in Neurology; 10(5):377-385; Sep. 2008.
Boggioa et al.; A randomized, double-blind clinical trial on the efficacy of cortical direct current stimulation for the treatment of major depression; International Journal of Neuropsychopharmacology; 11(2): 249-254; Mar. 2008.
Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar. 2004.
Fecteau et al.; Diminishing risk-taking behavior by modulating activity in the prefrontal cortex: a direct current stimulation study; J Neurosci.; 27(46):12500-5; Nov. 14, 2007.
Fitzgerald et al.; Transcranial magnetic stimulation in the treatment of depression: a double-blind, placebo-controlled trial; Arch Gen Psychiatry; 60(10):1002-8; Oct. 2003.
Fregni et al.; Anodal transcranial direct current stimulation of prefrontal cortex enhances working memory; Exp Brain Res.; 166(1); pp. 23-30; Sep. 2005.
Khedr et al.; Therapeutic effect of repetitive transcranial magnetic stimulation on motor function in Parkinson's disease patients; Eur J Neurol; 10(5):567-72; Sep. 2003.
Kleinjung et al.; Transcranial magnetic stimulation: a new diagnostic and therapeutic tool for tinnitus patients; Int Tinnitus J.; 14(2):112-8; Jul./Dec. 2008.
Lang et al.; Bidirectional Modulation of Primary Visual Cortex Excitability: A Combined tDCS and rTMS Study; Investigative Ophthalmology and Visual Science; 48(12): 5782-5787; Dec. 2007.
Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56(9): 634-639; Nov. 1, 2004.

(56) References Cited

OTHER PUBLICATIONS

Mansur et al.; A sham stimulation-controlled trial of rTMS of the unaffected hemisphere in stroke patients; Neurology; 64(10):1802-4; May 24, 2005.

Nitsche et al.; Excitability changes induced in the human motor cortex by weak transcranial direct current stimulation; Journal of Physiology; 527(3):633-639; Sep. 15, 2000.

O'Reardon et al.; Efficacy and safety of transcranial magnetic stimulation in the acute treatment of major depression: a multisite randomized controlled trial; Biol Psychiatry; 62(11):1208-16; Dec. 1, 2007.

Ragert et al.; Improvement of spatial tactile acuity by transcranial direct current stimulation; Clin. Neurophysiol.; 119(4):805-11; Apr. 2008 (author manuscript).

Roizenblatt et al.; Site-specific Effects of Transcranial Direct Current Stimulation on Sleep and Pain in Fibromyalgia: A Randomized, Sham-controlled study; Pain Practice; 7(4): 297-306; Dec. 7, 2007.

Sparing et al.; Enhancing language performance with non-invasive brain stimulation R A transcranial direct current stimulation study in healthy humans; Neuropsychologia; 46(1): 261-268; Jan. 15, 2008.

Theodore et al.; Transcranial magnetic stimulation for the treatment of seizures: a controlled study; Neurology; 59(4):560-2; Aug. 27, 2002.

Schneider et al.; U.S. Appl. No. 12/912,650 entitled "Sub-motor-threshold stimulation of deep brain targets using transcranial magnetic stimulation," filed Oct. 26, 2010.

Mishelevich et al.; U.S. Appl. No. 12/990,235 entitled "Transcranial magnetic stimulation by enhanced magnetic field perturbations," filed Oct. 29, 2010.

Mishelevich et al.; U.S. Appl. No. 12/917,236 entitled "Treatment of clinical applications with neuromodulation," filed Nov. 1, 2010.

Blount et al.; The Influence of Thyroid and Thiouracil on Mice Exposed to Roentgen Radiation; Science; 109(2822); pp. 83-84; Jan. 28, 1949.

Buxton; Pharmacokinetics and Phamacodynamics; Goodman & Gilman's the Pharmacological Basis of Therapeutics (11th Ed.); McGraw-Hill, © 2006; pp. 1-23; pub. date Oct. 28, 2005.

George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.

Kimeldorf et al.; The effect of exercise upon the lethality of roentgen rays for rats; Science; 112(2902); pp. 175-176; Aug. 1950.

Lemaire et al.; Influence of blood components on the tissue uptake indices of cyclosporin in rats; J Pharmacol Exp Ther; 244(2); pp. 740-743; Feb. 1988.

Rubin et al.; Radiosensitivity and radioresistance of tumors; Clinical Radiation Pathology; WB Saunders; Ch. 24, pp. 894-933; Jun. 1968.

Rubin et al.; The Modification of Radiation Response; Clinical Radiation Pathology; WB Saunders; Ch. 26, pp. 973-1008; Jun. 1968.

Smith et al.; Effect of thyroid hormone on radiation lethality; Am J Physiol; 165(3); pp. 639-650; Jun. 1951.

Ueno; Individual differences in radio sensitivity of mice correlated with their metabolic rate; Acta Radiol Ther Phys Biol; 10(4); pp. 427-432; Aug. 1971.

Schneider et al.; U.S. Appl. No. 13/877,428 entitled "Transverse transcranial magnetic stimulation coil placement for improved analgesia," filed Apr. 2, 2013.

Schneider et al.; U.S. Appl. No. 14/131,223 entitled "Concurrent stimulation of deep and superficial brain regions," filed Jan. 7, 2014.

\* cited by examiner

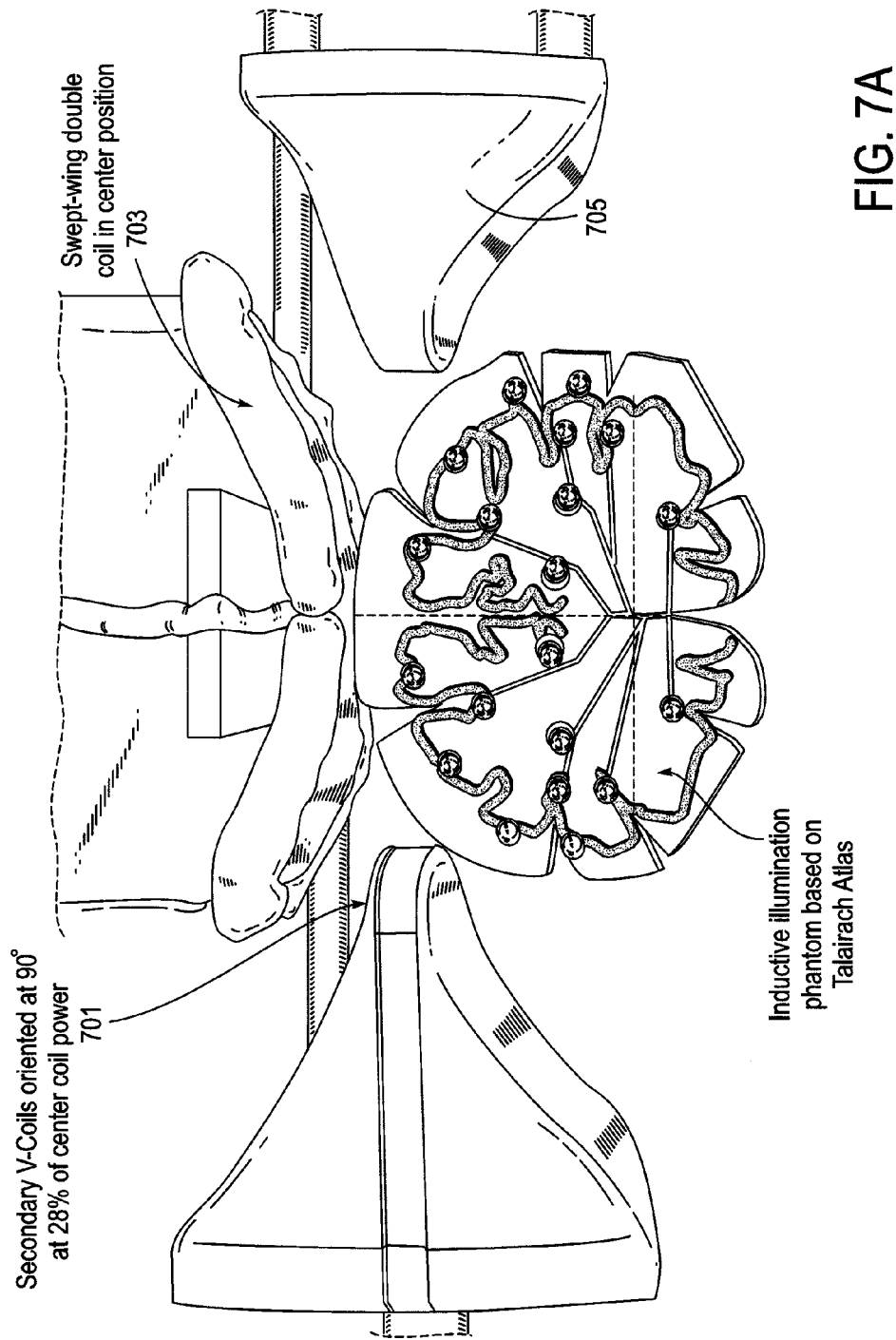

Coil Powers: Center 25%, Left 10%, Right 10%, Top 25%
3D Phantom in Diamond Array Coil Powers: Center 80%, Left 60%, Right 80%, Top 25%
3D Phantom in Diamond Array

FIG. 10

| Subject # | Array polarity | Motor Threshold[1] | Highest Coil Percentage Powers used[2] (top/left/right/front) | Results |
|---|---|---|---|---|
| 1 | Side and front coils in opposite polarity with respect to top coil | 80% | 65/30/30/65 | Preferential cingulate suppression and analgesia |
| 2 | | 85% | 70/40/40/70 | Preferential cingulate suppression and analgesia |
| 3 | | 90% | 99/75/75/90 | Preferential cingulate suppression plus analgesia. Best case. |
| 4 | | 55% | 60/60/60/60 | Non-preferential suppression of cingulate plus analgesia |
| 5 | | 75% | 82/82/82/82 | Preferential cingulate up-regulation and hyperalgesia |
| 6 | | 100% | 60/50/50/45 | Non-preferential suppression o f cingulate plus analgesia |
| 7 | | 70% | 70/70/70/50 | Non-preferential suppression o f cingulate plus analgesia |
| 8 | | 70% | 70/60/60/35 | Preferential cingulate suppression plus analgesia. |
| 9 | | 90% | 80/55/55/55 | Non-preferential suppression o f cingulate plus analgesia |
| 10 | | 75% | 55/55/55/55 | Non-preferential cingulate up-regulation and hyperalgesia |
| 14 | 4 coils in same polarity | 90% | 50/30/30/30 | Hyperalgesia. Imaging results TBD |
| 15 | | 80% | 50/25/25/10 | Hyperalgesia. Imaging results TBD |

[1] Percentage refers to the percent of the maximum power output.
[2] Numbers are percent of total power (i.e., percent of maximum output) for each TMS electromagnet.

TRANSCRANIAL MAGNETIC STIMULATION FIELD SHAPING

CROSS REFERENCE TO RELATED APPLICATIONS

This patent application claims priority as a continuation-in-part of U.S. National Phase patent application Ser. No. 12/670,938, filed on Jun. 17, 2010, titled "FIRING PATTERNS FOR DEEP BRAIN TRANSCRANIAL MAGNETIC STIMULATION", which claims priority to PCT Patent Application No. PCT/US2008/073751, filed on Aug. 20, 2008, which claims priority to U.S. Provisional Patent Application No. 60/956,920, filed on Aug. 20, 2007, U.S. Provisional Patent Application No. 60/970,958, filed on Sep. 9, 2007, and U.S. Provisional Patent Application No. 61/077,488, filed on Jul. 2, 2008.

This patent application also claims priority as a continuation-in-part of U.S. patent application Ser. No. 12/701,395, filed on Feb. 5, 2010, titled "CONTROL AND COORDINATION OF TRANSCRANIAL MAGNETIC STIMULATION ELECTROMAGNETS FOR MODULATION OF DEEP BRAIN TARGETS", which claims priority as a continuation-in-part to PCT Patent Application No. PCT/US2008/075575, filed on Sep. 8, 2008, which claims priority to U.S. Provisional Patent Application No. 60/970,534, filed on Sep. 7, 2007; 60/970,532, filed on Sep. 7, 2007; and 60/975,177, filed on Sep. 26, 2007.

This patent application also claims priority as a continuation-in-part of U.S. patent application Ser. No. 12/185,544, filed on Aug. 4, 2008, titled "MONOPHASIC MULTI-COIL ARRAYS FOR TRANSCRANIAL MAGNETIC STIMULATION", which claims priority to U.S. Provisional Patent Application No. 60/954,018, filed on Aug. 5, 2007.

This patent application also claims priority as a continuation-in-part of U.S. patent application Ser. No. 12/324,227, filed on filed Nov. 26, 2008, titled "TRANSCRANIAL MAGNETIC STIMULATION OF DEEP BRAIN TARGETS", which claims priority to U.S. Provisional Patent Application No. 60/990,300, filed on Nov. 27, 2007 and U.S. Provisional Patent Application No. 60/992,385, filed on Dec. 5, 2007.

This patent application also claims priority to U.S. Provisional Patent Application No. 61/227,000, filed on Jul. 20, 2009, titled "TMS FIELD SHAPING".

Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are devices, systems and methods for Transcranial Magnetic Stimulation (TMS) including a primary TMS electromagnet and one or more secondary TMS electromagnets arranged and configured to focus the magnetic flux in a target brain region and to limit or decrease the induced current in non-target brain regions.

BACKGROUND OF THE INVENTION

Transcranial Magnetic Stimulation (TMS) is typically delivered using an electromagnet positioned at the side of the head, the top of the head, or somewhere in between the side and the top of the head. Generally speaking, a single or double standard TMS coil placed on a patient's scalp and operated at a power level at, or slightly above, a patient's motor threshold will directly active neurons from the cortical crowns to the bottom of the cortical gyri—a depth of about 1-3 cm. Using this approach, deeper structures (herein referred to as "subcortical", even when these deeper areas are histologically layered in nature) are activated only secondarily through intracerebral neural connections. Conventional TMS approaches typically do not reach greater depths. For example, the cingulate gyms, the insula and other subcortical structures are generally not directly accessible for modulation traditional TMS without causing overstimulation of non-target (e.g., more superficially located regions) which may lead to pain and discomfort for the patient). Deep brain modulation cannot be accomplished by simply turning up the power of the stimulating electromagnet, because the intervening tissue, including superficial cortex, will be over-stimulated, causing undesired side effects such as seizures.

Positive outcomes for treatment of depression refractory to drug treatment have been demonstrated with repetitive Transcranial Magnetic Stimulation (rTMS, Avery et al., 2005). rTMS works indirectly, because the superficial stimulation of the dorsolateral pre-frontal cortex is carried by nerve fibers to the deeper cingulate gyms. More effective therapy of depression and treatment of a number of other conditions such as chronic pain, addiction, obesity, and obsessive compulsive disorders may be possible with focused brain stimulation that is capable of reaching depths below the cortex. Devices for providing deep brain stimulation with Transcranial Magnetic Stimulation are described in Schneider and Mishelevich, U.S. Pat. No. 7,520,848 and Mishelevich and Schneider, U.S. patent application Ser. No. 11/429,504. Whether superficial or deep stimulation is being employed, focusing the applied magnetic field during TMS has the potential to improve clinical results. In particular, the ability to stimulate at depth could be facilitated by shaping the profile of the magnetic field of one or more primary stimulating electromagnets, thereby focusing their magnetic fields and more preferentially stimulating a given targeted neural structure.

The magnetic fields used for Transcranial Magnetic Stimulation typically determine both the depth and the size of the region of stimulation. Thus, a more focused magnetic field may be capable of stimulating an area that is also more tightly focused, and may be better controlled by the TMS system.

Transcranial magnetic stimulation of deeper brain regions would benefit from improved focusing of the magnetic field of the primary stimulating electromagnets. Described herein are systems, methods and devices for improving the focus of the primary electromagnets used for Transcranial Magnetic Stimulation, and may allow enhanced stimulation of targeted neural structures.

SUMMARY OF THE INVENTION

Described herein are devices, systems and methods for Transcranial Magnetic Stimulation (TMS). In particular, described herein are systems and devices including a plurality of TMS electromagnets having at least one primary TMS electromagnet and one or more (e.g., two, three, four, etc.) secondary TMS electromagnets that are arranged and configured so that the secondary TMS electromagnet(s) focus the flux of the primary electromagnet. The secondary TMS electromagnet(s) may focus the primary TMS electromagnet by emitting a magnetic field that is concurrent with the magnetic field emitted by the primary TMS electromagnet, which may be opposite in polarity.

In general, field shaping of the magnetic (electromagnetic) field emitted by the TMS devices and systems described herein may allow focusing and deep-brain penetration. Field shaping may be achieved by: the relative positions of the primary and secondary TMS electromagnets; the type (configuration) of the primary and secondary TMS electromagnets; and the relative powers of the primary and secondary TMS electromagnets (both the relative powers applied and the relative magnitudes of the emitted magnetic fields from the primary and secondary TMS electromagnets). These factors are described in greater detail herein. For example, the devices and systems described herein may be configured so that the primary TMS electromagnet is positioned between two or more secondary TMS electromagnets around the surface of a patient's head. The primary and secondary TMS electromagnets may be positioned so that the central axis of the emitted magnetic field of each secondary TMS electromagnet is directed towards the same deep brain target as the primary TMS electromagnet, or at a different (e.g., adjacent) deep brain target. The system or device may include a frame or support structure (e.g., a gantry) for holding the primary and secondary TMS electromagnets in position around the subject's head.

As mentioned, the secondary TMS electromagnets may be configured to emit a magnetic field that has a lower magnitude than the primary TMS electromagnet. For example, the secondary TMS electromagnets may be powered at a fraction (e.g., 95%, 90%, 85%, 80%, 75%, 70%, 65%, 60%, 55%, 50%, 45%, 40%, 35%, 30%, etc.) of the power applied to the primary TMS electromagnet. For example, the emitted magnetic field from the primary TMS electromagnet may be on the order of 1-2 Tesla (near the surface of the TMS electromagnet), and the emitted magnetic field from a secondary TMS electromagnet may be between 5 and 90% (e.g., 10-80%, 40-80%, etc.) of the primary TMS electromagnet, for example, 0.2 Tesla.

Different configurations of TMS electromagnets are also described herein. For example, the primary TMS electromagnet may be a swept-wing coil and the secondary TMS electromagnets maybe V-shaped coils, as described in greater detail below.

Thus, described herein are Transcranial Magnetic Stimulation (TMS) systems for stimulating a neuronal tissue, and particularly for stimulation of one or more deep-brain targets by shaping the emitted magnetic field of a primary TMS electromagnet using one or more secondary TMS electromagnets. For example, a TMS system (or TMS device) may include: a primary TMS electromagnet configured to apply Transcranial Magnetic Stimulation to the subject; a plurality of secondary TMS electromagnets configured to shape the magnetic field emitted by the primary TMS electromagnet. The secondary TMS electromagnets are configured for stimulation at a lower power than the primary TMS electromagnet to emit a magnetic field that is concurrent with, and shapes, the magnetic field emitted by the primary TMS electromagnet. In some variations the secondary TMS electromagnets are configured to be stimulated at the same power as the primary TMS electromagnet(s).

In variations in which multiple secondary electromagnets are used, the secondary TMS electromagnets may be controlled (and powered) together, or individually or in sub-sets. For example, the secondary TMS electromagnets may be driven by the same power source (which may be separate or different from the power source for the primary TMS electromagnet), and all or a subset of the secondary TMS electromagnets may be powered to the same level. For example, the secondary TMS electromagnets (or a subset of them) may both be powered to 50% of the level of the primary TMS electromagnet.

These systems may also include a controller for controlling the power applied to the secondary and/or primary TMS electromagnets. For example, a controller may limit the power applied to the secondary TMS electromagnets so that they apply a fraction of the power applied by the primary TMS electromagnet. The controller may be configured to apply balanced power, for example, by applying the same power to the secondary TMS electromagnets in similar positions relative to the primary TMS electromagnet (e.g. on either side of the primary TMS electromagnet). In some variations the controller may apply power by applying current to the secondary TMS electromagnets that is opposite in polarity to the primary TMS electromagnet(s).

Reducing the current (power) applied to the secondary TMS electromagnets (which may be referred to as 'side coils') compared to the primary TMS electromagnet(s) may enhance focusing of the emitted field. Reducing the power applied to the secondary TMS electromagnets may also reduce or prevent pain or discomfort experienced by a subject undergoing TMS. Reducing the power applied to the secondary TMS electromagnets may also reduce the stimulation of non-target tissue regions, including more cortical regions (e.g., regions intermediate to the target), and sensory nerves of the orbit and sinuses. For example, PCT/US2008/073751, previously incorporated by reference, describes one such system. In variations in which a "front" secondary TMS electromagnet is used, such as a secondary TMS electromagnet that is positioned over the subjects facial region (e.g., forehead, eyes, nose, etc.) the patient, the power applied may be less than the other secondary TMS electromagnets.

In some variations, the secondary TMS electromagnets may limit or decrease the induced current in adjunct non-target regions while only slightly decreasing the induced current in the target tissue. In other variations, the secondary TMS electromagnets may increase the magnetic field of the primary TMS electromagnet(s). As described herein, a magnetic field may be shaped by constructive magnetic interference or by destructive magnetic interference. For example, a magnetic shaping may occur by reduction of field strength, and magnetic field shaping may occur by augmentation of field strength. For example, improved focusing may be achieved with overall field reduction using two lateral TMS electromagnet coils fed with a reduced current (relative to a center coil) of opposite polarity. This may be referred to as "subtractive" summing of the array. In other variations, increased field strength at depth within the brain may be produced by having adjacent TMS electromagnets of the same polarity. This may be referred to as "additive" summary of the array. An array of primary and secondary TMS electromagnets may be operated in either additive (same polarity of primary and secondary TMS electromagnets) or subtractive (opposite polarity between primary and secondary TMS electromagnets) modes. Magnetic polarity may be changed by altering the polarity of the electrical wiring (e.g., within a controller), or by physically repositioning the coils.

For example, a three-coil (e.g., "triad") configuration may be operated so that the secondary TMS electromagnets have the opposite polarity to the primary TMS electromagnet. A four coil (e.g., "diamond") configuration may be operated additively, so that the secondary TMS electromagnets have the same polarity as the primary TMS electromagnets.

In some variations, the adjacent TMS electromagnets ('lateral' TMS electromagnets, typically secondary TMS electromagnets) may be use with current that is greater or equal to the current applied to the primary (central) TMS electromagnet.

Also described herein are Transcranial Magnetic Stimulation (TMS) systems for stimulating a subject's neuronal tissue that include: a primary TMS electromagnet configured to apply Transcranial Magnetic Stimulation to the subject; and at least one secondary TMS electromagnet configured to shape the magnetic field emitted by the primary TMS electromagnet, and the secondary TMS electromagnet is configured for stimulation at a lower power than the primary TMS electromagnet to emit a magnetic field that is of opposite polarity and is concurrent with and shapes the magnetic field emitted by the primary TMS electromagnet.

In general, the secondary TMS electromagnets may be at a lower power than the primary TMS electromagnets, and they may be at different powers relative to each other. For example, in variations including multiple secondary TMS electromagnets, the secondary TMS electromagnets may each be powered to a different level (and may each be lower than the primary TMS electromagnet) or a subset of the secondary TMS electromagnets (or all of them) may be powered to the same level.

Also described herein are Transcranial Magnetic Stimulation (TMS) systems for stimulating a subject's neuronal tissue that include: a primary TMS electromagnet configured to apply Transcranial Magnetic Stimulation to the subject; a plurality of secondary TMS electromagnets configured to shape the magnetic field emitted by the primary TMS electromagnet, wherein the secondary TMS electromagnets are configured be stimulated at a lower power and to emit a magnetic field that is opposite in polarity and concurrent with the magnetic field emitted by the primary TMS electromagnet, and wherein the primary TMS electromagnet is configured to be positioned between the secondary TMS electromagnets around the patient's head.

The primary TMS electromagnet and the secondary TMS electromagnets may be two-coil TMS electromagnets having different geometries. In some variations, the primary TMS electromagnet is a flat-bottomed TMS electromagnet and the secondary TMS electromagnets are V-shaped TMS electromagnets.

As mentioned, any of the systems and devices described herein may include a controller configured to coordinate the application of power to the primary and secondary TMS electromagnets. The systems or devices may also include a frame configured to secure the primary and secondary TMS electromagnets so that the primary TMS electromagnet is positionable between the secondary TMS electromagnets around a patient's head.

In some variations the systems or devices include three secondary TMS electromagnets. For example, the system may include a primary ("top") TMS electromagnet and two lateral ("side") secondary TMS electromagnets that are positioned at approximately a 90 degree angle relative to the primary TMS electromagnet. A third ("front") secondary TMS electromagnet may also be included. In operation, the patient is positioned and the primary and secondary TMS electromagnets are positioned around the outside of the patient's head.

Also described herein are devices for performing Transcranial Magnetic Stimulation (TMS) comprising: a primary TMS electromagnet configured to apply Transcranial Magnetic Stimulation to a subject; a plurality of secondary TMS electromagnets arranged around the primary TMS electromagnet and configured to shape the magnetic field emitted by the primary TMS electromagnet, wherein the secondary TMS electromagnets are configured to emit a magnetic field that is opposite in polarity and concurrent with the magnetic field emitted by the primary TMS electromagnet; and a frame configured to secure the primary and secondary TMS electromagnets in position around a subject's head so that the primary TMS electromagnet is between the secondary TMS electromagnets around the subject's head.

The device may include three secondary TMS electromagnets flanking the primary TMS electromagnet. As used herein the term "between" in reference to the spatial relationship of the primary and secondary TMS electromagnets refers to the relative positions of the TMS electromagnets around the outside of a patient's head when in use. None of the TMS electromagnets (primary or secondary) are positioned between another TMS electromagnet and the surface of the patient's head. In addition, both the primary and secondary TMS electromagnets are configured for and capable of TMS from outside of the subject's head (e.g., through the skin, skull, etc.). The primary and secondary TMS electromagnets are configured to generate a sufficiently powerful magnetic field to induce current in one or more target brain regions when stimulation is applied externally to the subject's head.

Also described herein are methods of performing TMS, and methods of shaping a magnetic field emitted by a primary TMS electromagnet. For example, described herein are methods of performing Transcranial Magnetic Stimulation (TMS) of target deep brain structures by shaping the field emitted by a primary TMS electromagnet, the method comprising: positioning a primary TMS electromagnet between a plurality of secondary TMS electromagnets around a subject's head; shaping the magnetic field emitted by the primary TMS electromagnet to modulate a deep brain target by simultaneously emitting a magnetic field from the primary TMS electromagnet and each of the plurality of secondary TMS electromagnets, wherein the energy applied to each of the secondary TMS electromagnets is less than the energy applied to the primary TMS electromagnet. The magnetic field emitted by the secondary TMS electromagnets may have the opposite polarity of the primary TMS electromagnet. The In some variations, the method includes the step of aiming the primary TMS electromagnet at a deep brain target within a subject's brain. The secondary TMS electromagnets may be aimed at a site that is not the deep brain target. For example, the TMS electromagnets may be aimed at a site that is displaced from the deep brain target (e.g., adjacent to it, etc.). As used herein "aiming" may refer to positioning the TMS electromagnet so that a vector perpendicular to the "face" of the TMS electromagnet, which typically corresponds to the primary axis or vector of an emitted magnetic field from the TMS electromagnet, is directed towards a target, such as the center of a deep brain target.

BRIEF DESCRIPTION OF THE DRAWINGS

FIG. 2 shows a top view of a model of a subject's head.

FIGS. 3 and 4 show various side projections or cross-sections through the subject's head indicating the placement and potential targets of the TMS electromagnets.

FIGS. 7A-7F illustrate testing of the field shaping of a primary TMS electromagnet by two secondary TMS electromagnets using a phantom (model) similar to the one shown in FIG. 6 to illustrate the effect of field shaping.

FIG. 10 is a table illustrating the effect of field shaping in an in vivo trial.

DETAILED DESCRIPTION OF THE INVENTION

Figure 1A:
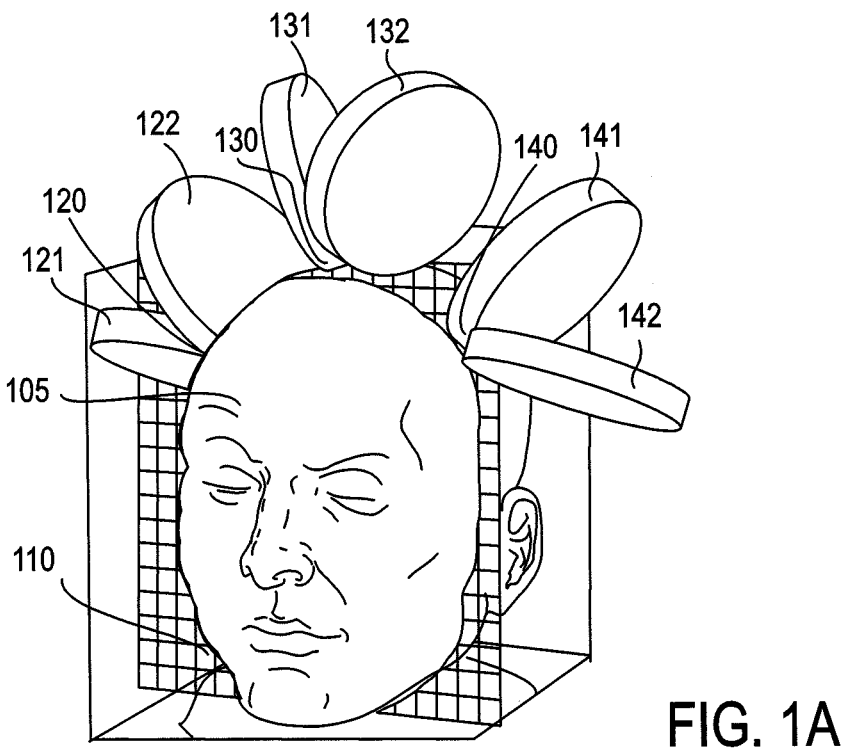
FIG. 1 shows an example of a system having an array of three TMS electromagnets (A, B, and C) positioned around a patient's head, shown in frontal external view (left), and in cross section (right).

Described herein are Transcranial Magnetic Simulation (TMS) systems and methods of using them for emitting focused, or shaped, magnetic fields for TMS. In particular, described herein are arrays (e.g., two-, three-, four-, five-, etc. coil arrays) of TMS electromagnets comprising at least one primary (e.g., central) TMS electromagnet and one or more (e.g., a plurality) of secondary TMS electromagnets. The secondary TMS electromagnets may be arranged around a primary TMS electromagnet, and are typically configured to be concurrently and/or synchronously fired with the primary TMS electromagnets to shape the resulting magnetic field and focusing it. The power applied to the primary and secondary TMS electromagnets may be independently controlled. This focusing may prevent or reduce stimulation of adjacent non-target brain regions. The secondary TMS electromagnets may also be oriented away from the target. For example, the secondary TMS electromagnets may not be aimed directly at the target, but may have an axis of the emitted magnetic field that is oriented towards the primary magnet (or elsewhere).

For example, described herein are systems and methods of using an array of TMS electromagnets including at a primary (e.g., central) TMS electromagnet and a plurality of secondary (e.g., lateral or surrounding) TMS electromagnets. Any of these TMS electromagnets may be referred to as "coils" or "magnets". The primary and secondary electromagnets may operate together to focus and enhance the signal emitted by the primary TMS electromagnet, so that that the resulting emitted field is narrower (e.g., less likely to induce substantial current in adjacent non-target regions) and may have increased power, particularly when compared to primary TMS electromagnets alone. The system including primary and secondary TMS electromagnets may be referred to as a "focusing array" of TMS electromagnets, or just an "array".

In some of the variations shown and described herein, the system includes one primary TMS electromagnet and two lateral secondary TMS electromagnets. This arrangement (described in more detail below) may be referred to as a "triad" or "triad array." Preliminary experiments suggest that a triad arrangement may result in an enhanced performance (focusing the shape and strength of the emitted magnetic field) which is greater than would be expected when compared to other arrangements of three TMS electromagnets (e.g., two adjacent TMS electromagnets), or readily predicted by summation/subtraction of the magnetic fields. Although the triad variations described herein include one primary and two secondary TMS electromagnets arranged substantially in a line or arc (as suggested by the term 'triad'), the secondary TMS electromagnets may be displaced from the primary (e.g., not in the same arc or line). Arrangements of more than three TMS electromagnets are also contemplated and described herein. For example, a primary TMS electromagnet may be surrounded by three, four, or five (or more) TMS electromagnets. The primary TMS electromagnets may be located at or near the center of the secondary TMS electromagnets, when the TMS electromagnets are positioned around the subject's head. The TMS electromagnets may be arranged in a plane or in a curved surface (e.g., conforming to the approximate curvature of the head).

In general, the primary TMS electromagnet is configured to emit the principle electromagnetic field, which is modified by the secondary electromagnet(s). The secondary TMS electromagnets may be a different type or configuration of TMS electromagnets. In one embodiment, both the primary and secondary TMS electromagnets are all double-coil (e.g., "figure-8") type TMS electromagnets; however, the shape of the TMS electromagnet may be modified. For example, the lateral TMS electromagnets may be V-shaped, curved, or flat-bottom V-shaped (e.g., "swept-wing" shaped). V-shaped coils are those in which the coils sweep outward at an angle to each other. Examples of different TMS electromagnet configurations may be found in PCT application PCT/US2008/075706 (WO 2009/033192), titled "FOCUSED MAGNETIC FIELDS" (filed Sep. 9, 2008), and in PCT Application No. PCT/US2010/020324, titled "SHAPED COILS FOR TRANSCRANIAL MAGNETIC STIMULATION", filed on Jan. 7, 2010.

In general, the magnetic field produced by each magnet in the array linearly sums with the field produced by the other magnets in the array, and that the net magnetic flux, as a function of time, will induce electrical current in intracerebral structures such as neurons depending upon their location, geometry and conductivity. This will produce effects within the neurons which may be desired or undesired. The shape of the TMS electromagnets, and their position within an array, as well as parameters such as the power to each magnet in the array can be calculated to induce flux in neurons where an effect is desired, and not to induce flux in neurons where an effect is not desired.

As mentioned, the secondary TMS electromagnet(s) may have a different shape than the primary TMS electromagnet. For example, the primary TMS electromagnet may be a flat bottomed TMS electromagnet coil, while the lateral secondary coils are V-shaped. A flat-bottomed coils is one in which the two coils meet in a planar region but then each spread back at an angle with the flat central region. The central region (the flat bottom region) may be positioned on or near the head closest to the target. The V-shaped coil is one in which the two coils forming the TMS electromagnet meet to form more of a point, rather than a flat region (although the "point" may be rounded). In some variations, the central regions of the coils are pressed flat against each other to produce an "I-bottomed" coil.

The system typically includes at least one primary TMS electromagnet and at least two secondary TMS electromagnets, as mentioned. The secondary TMS electromagnets may be arranged in a fixed configuration relative to the primary TMS electromagnet, or they may be movable (or adjustable) relative to each other. For example, in some variations the system includes a frame or connector linking the primary and secondary TMS electromagnets. This frame may be adjustable so that the angle and/or separation between the TMS electromagnets may be adjusted. In some variations, the adjustment of the separation between the TMS electromagnets may be coordinated so that the secondary TMS electromagnets are approximately equidistant from the primary TMS electromagnet (e.g., with the primary TMS electromagnet in the center). The primary and secondary TMS electromagnets may be approximately the same size (e.g., the same number of windings, etc.), or they may be different sizes (e.g., the primary TMS electromagnet may be larger than the secondary TMS electromagnets). As mentioned, the focus of the secondary TMS electromagnets (e.g., determined by the direction of a radial axis through the emitted field of the TMS electromagnet) may be different from the focus of the primary TMS electromagnet. In addition, each secondary TMS electromagnet may have an independent focus. The secondary TMS electromagnets may be focused on or towards the primary TMS electromagnet so that they may modify (constructively or destructively) a portion of the field emitted by the primary TMS electromagnet.

The stimulation of the primary and secondary TMS electromagnets may be coordinated and overlapping. For example, the primary and secondary TMS electromagnets may all fire at the same time. The secondary TMS electromagnets may be powered at a lower level (e.g., some percentage of the power applied to the primary TMS electromagnet). Thus, in some variations of the system, the primary and secondary TMS electromagnets are all connected to the same power supply, so that they may be controlled for synchronous firing. In some variations the secondary TMS electromagnets may be powered or driven by a separate power supply from the primary TMS electromagnet. A controller may be used to coordinate the firing of the primary and secondary TMS electromagnets. The controller may include a processor having control logic for synchronizing the firing and for controlling operation of the system or device.

The primary (e.g., central) TMS electromagnet and secondary (e.g., lateral or side) TMS electromagnet may be formed as part of the same circuit. The primary and secondary TMS electromagnets may be connected together in parallel or in series, such that they may be activated in unison by a single power source. Any appropriate power source may be used, for example, a capacitor bank having a single positive pole and a single negative pole. This embodiment may require a single power source that is substantially (e.g. three times) larger than a standard (e.g. Magstim™ Rapid) capacitor bank, since it must push adequate current despite the increased inductance of a single-complex-coil triad (or other) embodiment. Alternatively, the electromagnets can be powered by a plurality of power sources. A controller may coordinate activity of the plurality of power sources. For example, one commercially available power sources is the "Magstim Rapid$^2$" (Magstim Ltd., Wales, UK) power source that provides electrical currents for pulsed magnetic fields.

In some variations, the primary and secondary TMS electromagnets may be stimulated sequentially, but within a window of time to allow temporal summation of the magnetic fields on the tissue.

As described briefly above, the TMS electromagnets may be arranged and powered so that there is magnetic shaping to focus the emitted magnetic field by reducing the field strength of the primary electromagnet (e.g., by destructive electromagnetic interferences), and/or by augmentation of the field strength of the primary electromagnet (by constructive electromagnetic interference). The particular arrangements of the primary and secondary TMS electromagnets described herein make use of these general concepts of constructive and destructive interferences. As used herein, destructive interference may include or refer to the subtractive effect of magnetic fields applied to different TMS electromagnets. Similarly, constructive interference of magnetic fields may include or refer to the additive effect of separate magnetic fields. Thus, magnetic field shaping may occur by additive or subtractive effect of interacting magnetic fields.

In some variations, the emitted magnetic field of the primary TMS electromagnet may be shaped by laterally narrowing the emitted (e.g., "trimming" the sides of the emitted magnetic field). Although the application and system described herein should not be limited by any proposed theory of operation described herein, it may be the case that the primary TMS electromagnet magnetic field is shaped by reduction of the field strength of the magnetic field emitted by the primary TMS electromagnet by arranging the system so that the primary TMS electromagnet is stimulated at the opposite polarity of the secondary TMS electromagnets. Thus, adjacent fields may subtract from one another, and may cancel one another in a portion of the overlap zone. For example, when the primary TMS electromagnet is stimulated at a positive polarity (+), the secondary TMS electromagnets are stimulated at a negative (−) polarity.

As mentioned above, the primary TMS electromagnet may be surrounded by (e.g., immediately adjacent to) or centered between secondary TMS electromagnets. In some variations, the primary and secondary TMS electromagnets may be arranged linearly, within a curve, or in a substantially flat plane. In some variations the primary TMS electrode is positioned between multiple secondary coils around the outside of a subject's head. The system or device may include a frame to hold the TMS electromagnets in this position. The frame may be adjustable.

Shaping a magnetic field of the primary TMS electromagnet may be achieved in some variations by constructing the system so that the primary TMS electromagnet is stimulated at the same polarity to the secondary TMS electromagnets. In theory, the adjacent fields may add (sum) with one another, increasing the power in the overlap zone.

Examples

Figure 1B:
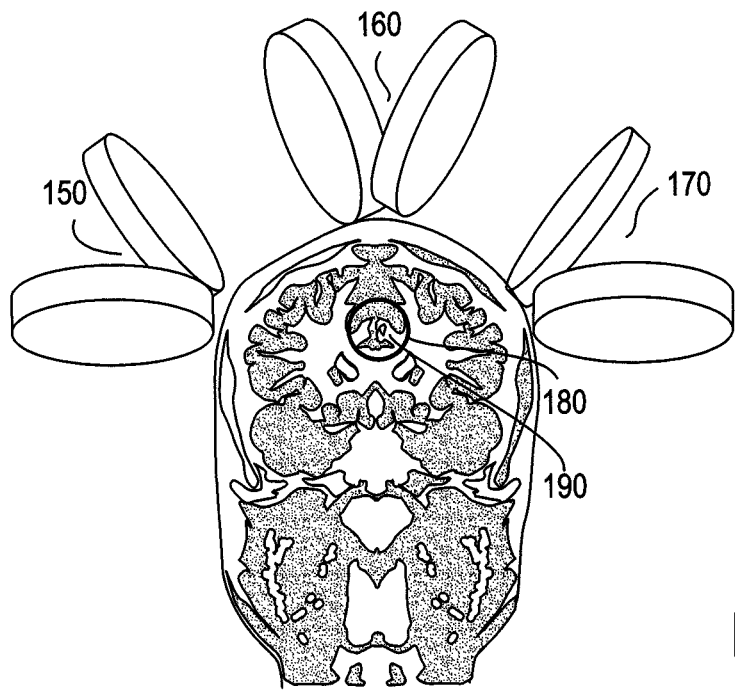

FIG. 1A shows one example of an array of three TMS electromagnet stimulator coils arranged around a patient's head. In this variation (which may be referred to as a triad array), the patients head 105 is shown transected by plane 110, which corresponds to the cross-section shown in FIG. 1B. The modified image shown is based in part on image data from Voxel-Man 3D Navigator. In FIGS. 1A and 1B, the V-shaped double coil 120 (also designated as coil A) is composed of circular coils 121 and 122, and bent at the center where the return path of the current in both coils is in the same direction. Similarly, V-shaped double coil 130 (also designated as coil B) is composed of circular coils 131 and 132 joined at a bent center, and V-shaped double coil 140 (also designated as coil C) is composed of circular coils 141 and 142, joined at a bent center. As described above, any of these coils may also be of other designs, for example flat double coils, flat-bottomed (swept-wing) V coils, or I-bottom V coils. Within target area 180 there is targeted anatomy 190. In this example, the target area is the left and right cingulum, shown circled in FIG. 1B, and the target anatomy is the cingulate fiber bundle 180. In other variations the electromagnets are not V-shaped, but may be traditional figure-8 double coils (e.g., a 70 mm double-coil configuration such as the Model 9925 from Magstim Ltd., Wales, UK). In some variations, the axes across the faces of the electromagnets are oriented in different directions.

The distance between the bottom of the nearest cortical sulcus and the underlying deep target is typically less than the distance between the physical coil centers. When this condition is true, the magnetic fields of the array may summate at the deep target to a greater degree than at the cortical surface. In some variations, the TMS electromagnets may be locked or fixed in position, or may be adjustable and lockable into position to maintain the arrangement described. Both the distance between the TMS electromagnets and/or the angle of the TMS electromagnets (either relative to each other or relative to the subject's head) may be adjusted or adjustable. In some variations the three (or more) TMS electromagnets, including the primary and secondary TMS electromagnets, may be adjusted as a unit. The secondary TMS electromagnets may be relative 'fixed' with respect to the primary TMS electromagnets, so that an operator may adjust the position of the TMS electromagnets by adjusting the position of the primary TMS electromagnet.

In theory, by pulsing one or more coils with a polarity that is opposite that of an adjacent coil, magnetic flux reaching some locations may be canceled or dampened. For example in FIG. 1B, if Coil 160 is reverse-biased with respect to coils 150 and 170, respectively, the medial aspect of the field emitted by coils 150 and 170 may be largely cancelled. Conversely, by pulsing one or more of the coils a polarity that is same that of an adjacent coil, magnetic flux reaching some locations may be augmented. As mentioned, the power applied to the secondary TMS electromagnets may be at a separate (greater or lesser) level than the power applied to the primary TMS electromagnet.

FIGS. 2-5 illustrates a triad configuration, showing two rows of triad arrays, one anterior (coil 1, side-coil 1L and side-coil 1R) and one posterior (coil 2, side-coil 2L and side-coil 2R). In some variations, only a single triad array is used (e.g., half of that shown in FIG. 2), and may be positioned in any appropriate location, based on the target. Alternatively, the triad may be moved relative to the target.

Figure 2:
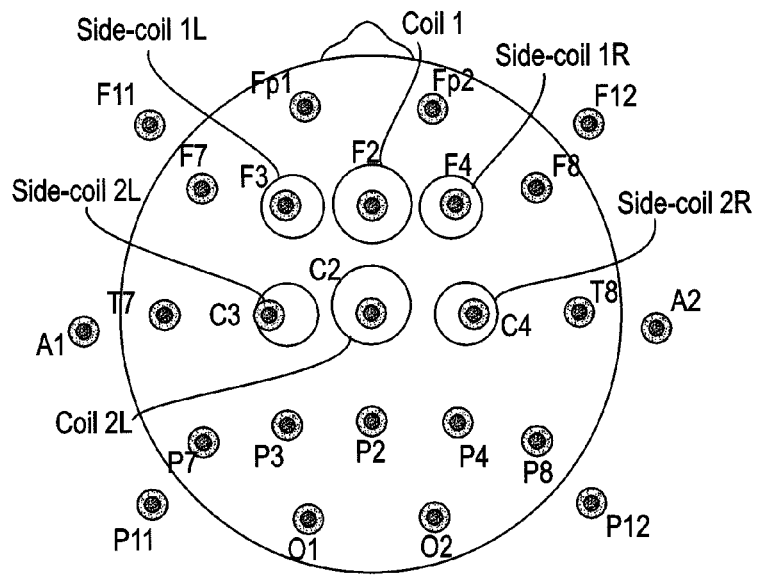
FIGS. 2-5 shows a variation of TMS electromagnet ("coil") placement in which there are two rows of "triad arrays", one anterior and one posterior.

In FIG. 2, the location of the coil centers for each TMS electromagnet are illustrated as circles and half-spheres. As this example regards a subtractive field-shaping approach, the side-coils are energized in opposite polarity with respect to the central coil. For example, in FIG. 2, primary coil 1 (at position "Fz") is flanked by secondary side-coil 1L, that is slightly medial to position F3, and by secondary side-coil 1R that is located slightly medial to position F4. The side coils (secondary coils) in this example, are typically powered at some level that is lower than the primary TMS electromagnet, and less (e.g., approximately 25% of) "MT". "MT" is the patient's motor threshold. Similarly, a second triad is also illustrated in FIG. 2. In this example, the primary coil, coil 2 at position Cz, is flanked by two secondary coils, side-coil 2L, which is located medial to position C3, and side-coil 2R, which is medial to position C4. As mentioned, these side-coils may be powered at less than the MT (e.g., 25% MT), typically in a polarity opposite the central coil. Each triad (composed of a main coil and two side-coils) may also be fired in sequence, so as to induce temporal summation at the target. By firing the front and back triad at separate times, mutual interference may be minimized.

As mentioned above, the secondary TMS electromagnets may be of the same type as the primary (central) TMS electromagnet (for example, a flat double coil, a flat-bottomed (swept-wing) V coil, or the "I-bottomed V"), but may also be of an alternative configuration in which both side coils are part of the same serial circuit, or with the main coil and the side-coils are loops of the same serial circuit of continuous wire.

In theory, when the side coils are positioned adjacent to the primary coil, and given opposite polarity to the center primary coil and equal power in each coil, the flux of the central coil may be so cancelled or compressed by the field of the lateral coils that if cannot reach the targets. One way of addressing the problem is to decrease the contribution of the lateral coils at opposite polarity to the center coil. Conversely, adjacent coils with the same polarity may create large areas of high magnetic flux. Thus, if different power is applied to different coils in an array, focality may be lost even as power levels within the brain are increased. Focality may be restored by balancing the power applied to each coil in the array in accordance with the conductivity and the geometry of the targeted structures as shown in the FIG. 8A-8D and the description herein.

Figure 3:
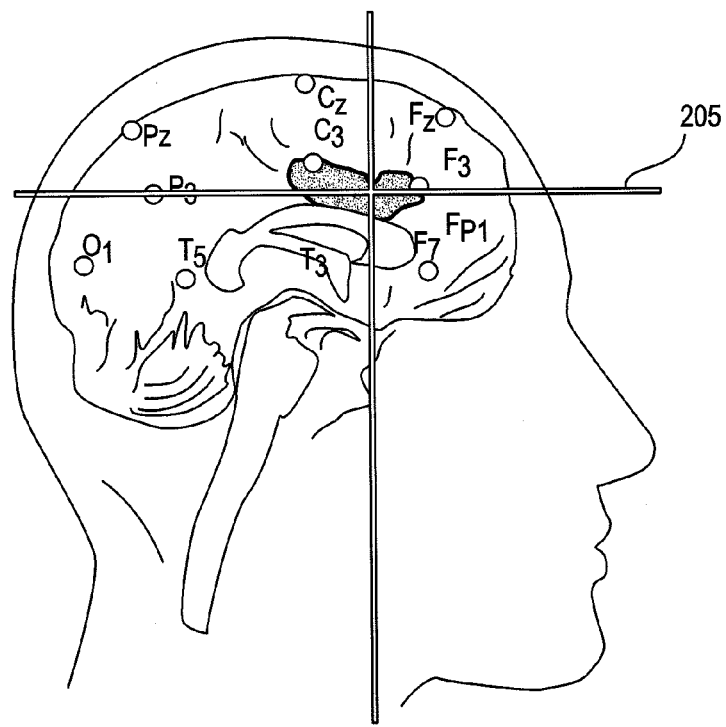
Figure 4:
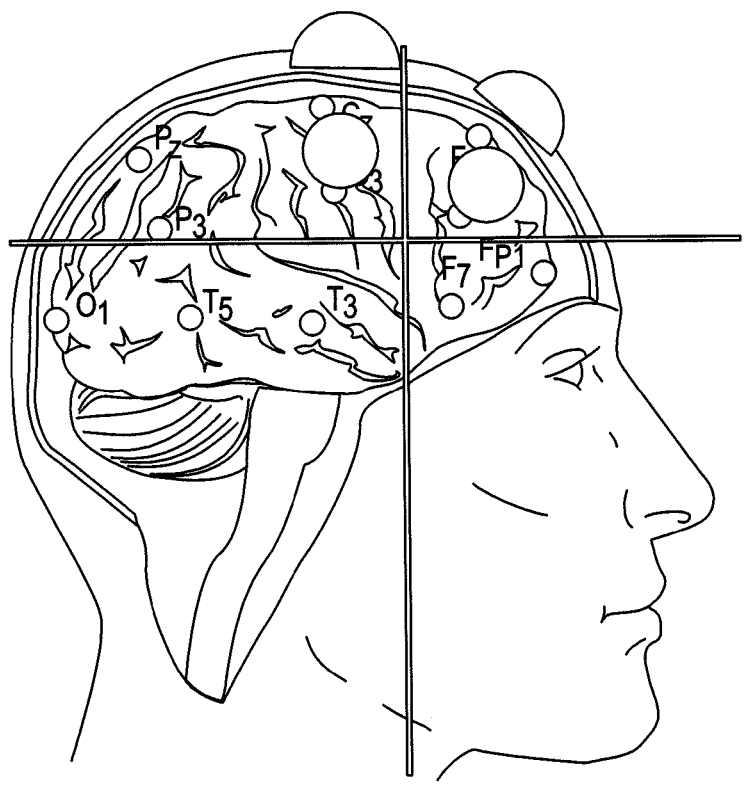
Figure 5:
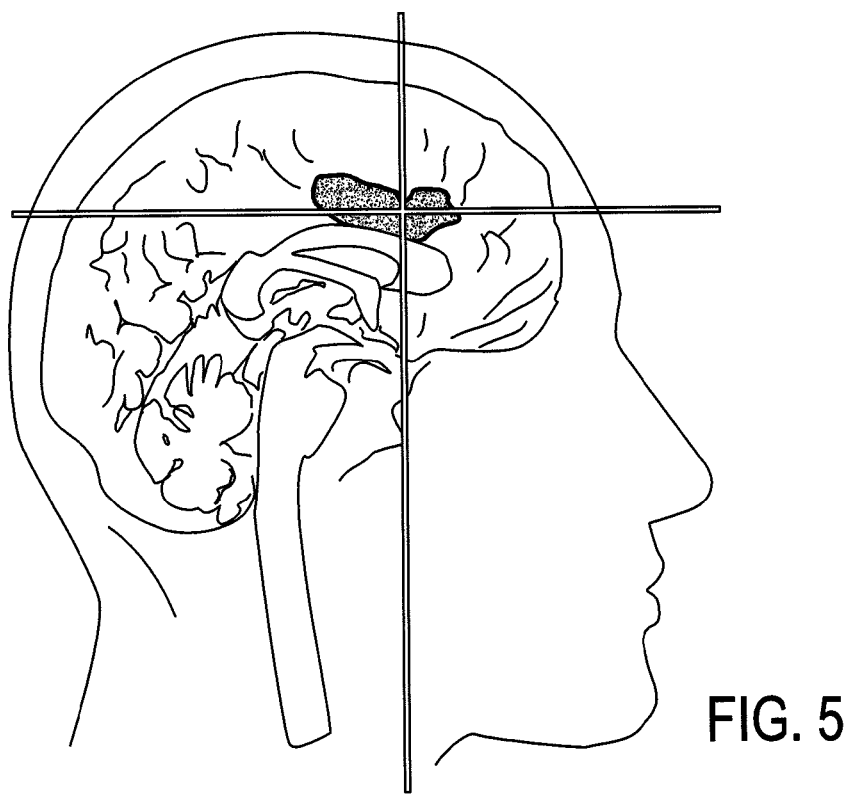

FIGS. 3 and 5 show a cross-sectional image through the subject's brain. The region of the brain about in the crosshairs 205 shown may represent the target region (e.g., the cingulum). FIG. 4 shows a side (partial cut-away) view of a patient's head in which the coil centers are shown against the head.

Figure 6:
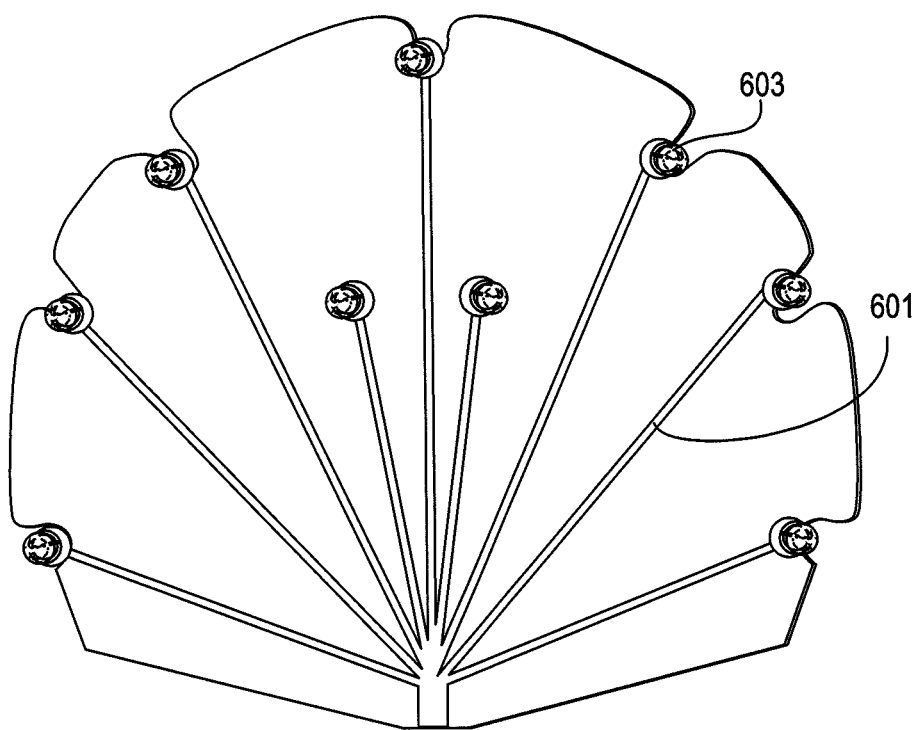
FIG. 6 shows one example of a model (phantom) which may be used to test the arrays described herein.

The configurations of the arrays (including the triad arrays) described above may be tested, including testing in models or phantoms. For example, FIGS. 6-7F illustrate variations of a "phantom" model and tests using the model. Tests with the phantom models described herein confirmed that focusing/shaping of the magnetic field of a primary TMS electromagnet by one or more secondary TMS electromagnets may occur sufficiently to stimulate deep-brain target regions.

FIG. 6 shows a simple model for illustrating field directionality and effect using the field shaping devices, systems and methods described herein. FIGS. 7A-7F illustrate another phantom model. In the model shown in FIG. 6, a two-dimensional form representing a section through the patient's brain is used and conductive pathways (e.g., insulated wires 601) are arranged in various orientations along a length of the model. The ends of the conductive pathways are connected to LEDs 603. Induced current along the pathways will result in activation of the LEDs, which can be seen as the LEDs light up. By arranging the conductive pathways (e.g., copper magnet wire) along the model in a way that mimics the conductive pathways of the brain, the model may reflect stimulation of some targets (e.g., neural tracts).

Figure 7B:
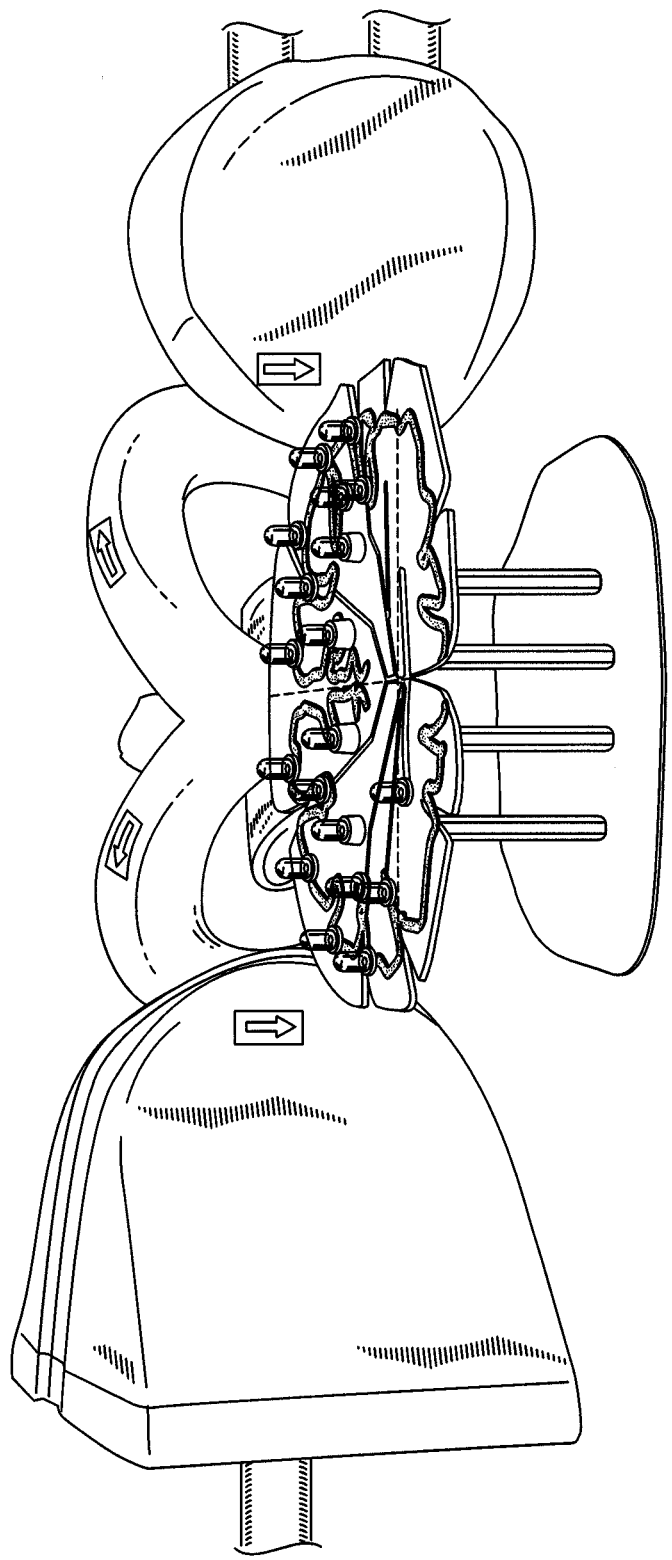
Figure 7C:
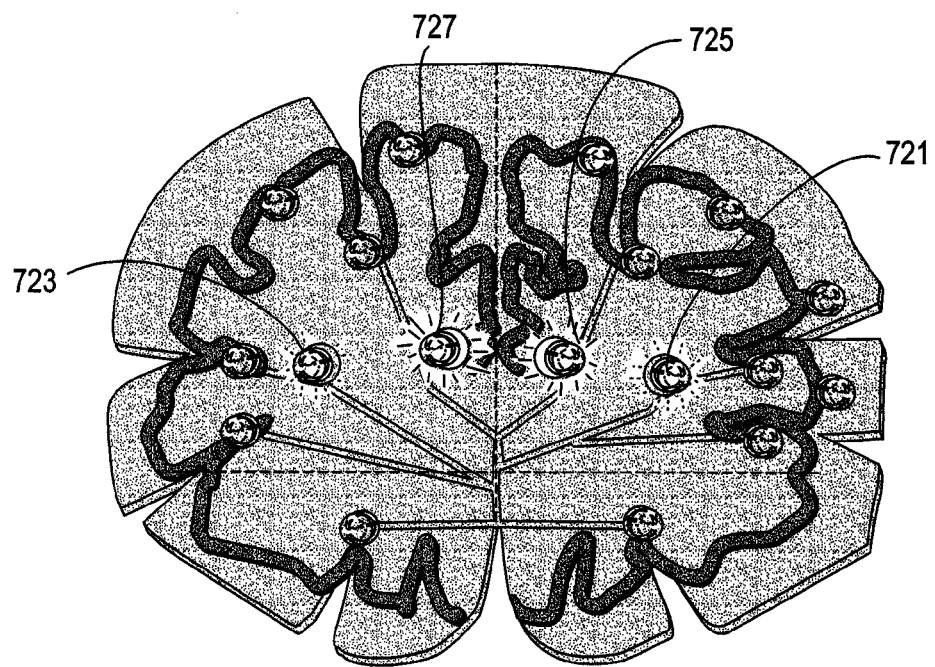
Figure 7D:
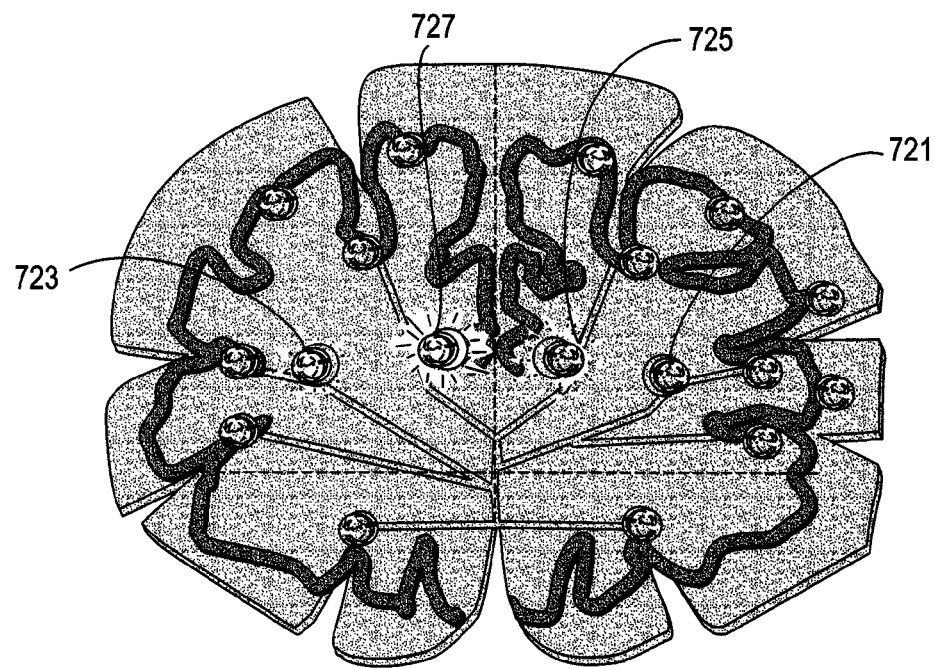
Figure 7E:
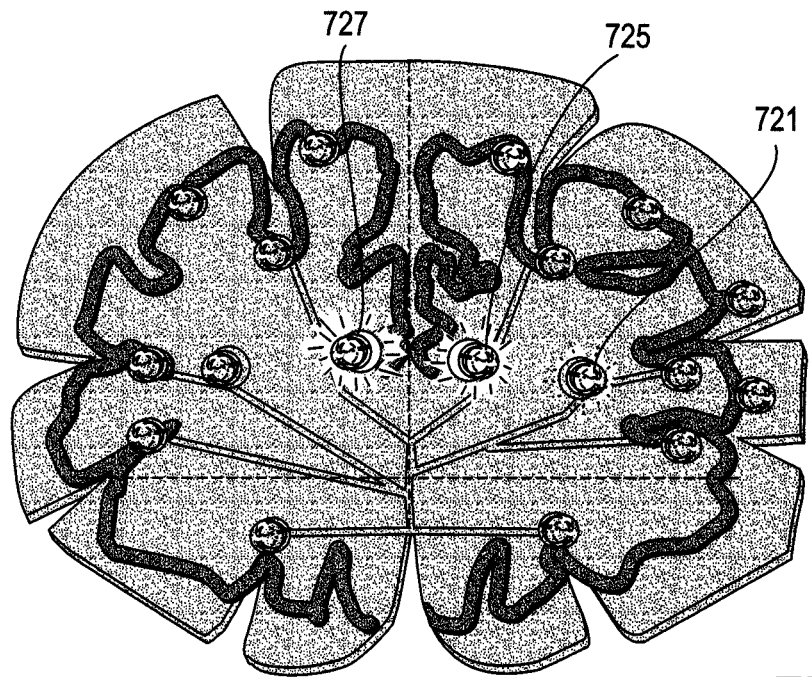
Figure 7F:
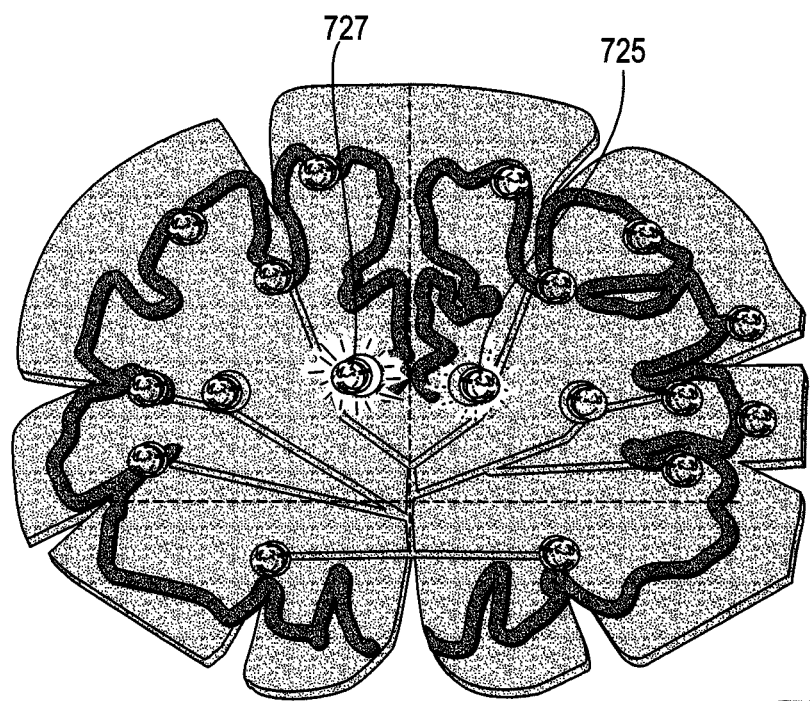

A slightly more refined model (based on the frontal brain tracts in a coronal section of a human brain, is used in FIGS. 7A-7F to test one variation of the triad configuration described herein. FIGS. 7A and 7B show a phantom model positioned between three TMS electromagnets 701, 703, 705. This phantom model is based on the Talairach Atlas of neuroanatomy, and includes tracts as well as at least two deep-brain targets. In FIGS. 7A and 7B the TMS electromagnets include a central primary TMS electromagnet 703, and two secondary TMS electromagnets 701, 705 oriented at 90 degrees to the primary TMS electromagnet. This arrangement is one variation of a triad configuration in which the secondary coils are configured differently than the primary coil. As shown in FIG. 7A, the primary coil 703 is a flat-bottomed (or I-bottomed) coil in which two coils include a substantially flat central region of contact between the two coils, and the non-contacting regions are swept back. The secondary coils 701, 705 are both V-shaped coils. The coils are aimed at a test target that is a two-dimensional brain section model having a plurality of LEDs connected to conductive pathways ("tracts") oriented similar to physiologic brain pathways. The two secondary TMS electromagnets oriented at approximately 90° to the primary TMS electromagnet may be stimulated (e.g., as shown in FIGS. 7D-7F, below) at 20% of the center coil power. In this example, all of the coils shown are hand-made experimental TMS electromagnets. Although the two secondary coils 701, 705 shown in FIG. 7B appear different in shape, both are I-bottomed V-shaped coils. In general, however, the side coils may have configurations that are different from each other and/or different from the primary coil, as mentioned above.

FIGS. 7C-7F illustrate the effect of the triad in focusing the emitted field. For example, FIG. 7C shows the target phantom model when only the primary (central) TMS electromagnet is activated, and the secondary TMS electromagnets are not active. In this example, four LEDs corresponding to both the target (the center two LEDs 727, 725) and non-target regions (lateral-most 2 LEDs 723, 721) are illuminated. The target LEDs are more brightly illuminated, corresponding to the strength of the induced current from the magnetic field.

In FIG. 7D the primary and left secondary TMS electromagnets are powered. The secondary TMS electromagnet is powered in the opposite polarity, and with a fraction of the power applied to the primary TMS electromagnet. FIG. 7D shows the right lateral (non-target) 721 LED is not illuminated at all, although the left lateral (non-target) LED 723 is illuminated. Both target LEDs 725, 727 are illuminated as well. FIG. 7E illustrates a similar effect when just the primary and right secondary TMS electromagnets activated, while the left secondary TMS electromagnet is not activated, resulting in activation of the right non-target LED 721 as well as the two target LEDs 725, 727. Finally FIG. 7F shows the focusing resulting from having both the primary and both secondary TMS electromagnets powered (e.g., the primary and both secondary TMS electromagnets). As shown in FIG. 7F, only the center two LEDs 725, 727 are illuminated, indicating that the emitted field has been focused or shaped by the secondary TMS electromagnets. The results of this phantom stimulation confirm that the secondary TMS electromagnets may shape, or focus, the primary TMS electromagnet, and emphasize the importance of the individual magnetic-field components, $B_x$, $B_y$, $B_z$ with their associated induced electrical currents in the target neuronal tissue.

Also described herein are methods for Transcranial Magnetic Stimulation of a neuronal target tissue. TMS may be performed by simultaneously applying a magnetic field to a target from a primary TMS electromagnet and two or more secondary TMS electromagnets that are oriented or configured as described herein. Such methods may be used to treat any disorder which may benefit from TMS, including depression and the like.

Figure 8A:
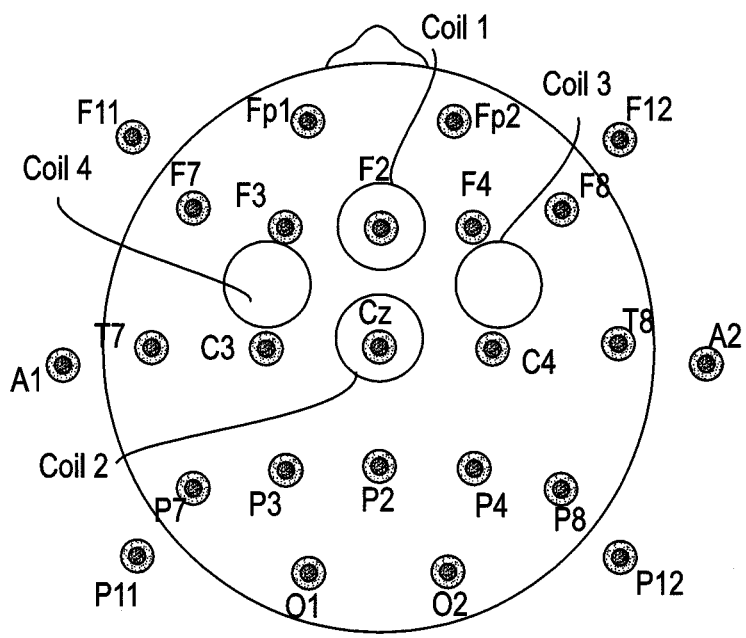
FIGS. 8A-8D illustrate a diamond-shaped configuration of four TMS electromagnets in which the constituent magnets may be operated in the same polarity and essentially the same orientation. This array may also be referred to as a "diamond array."
Figure 8B:
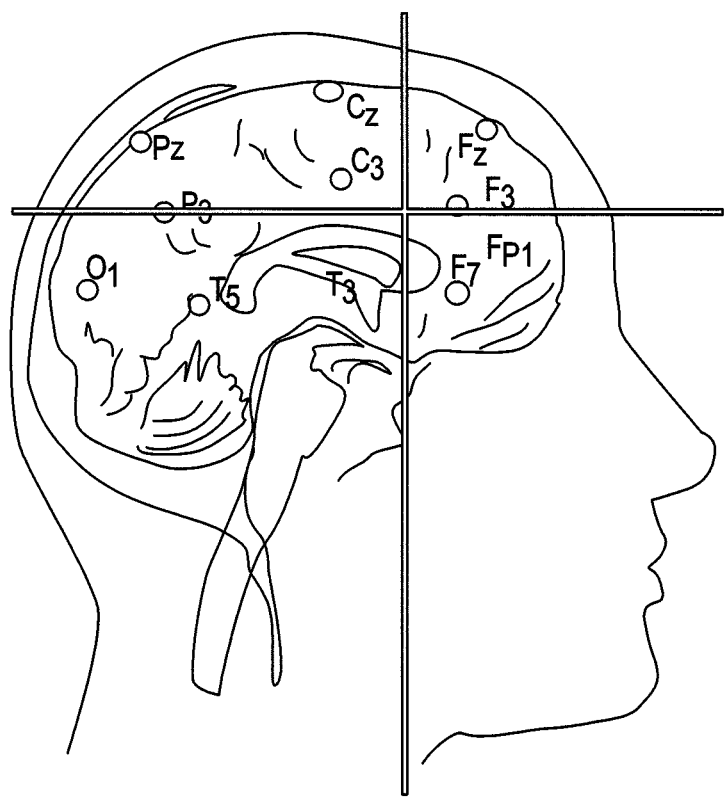
Figure 8C:
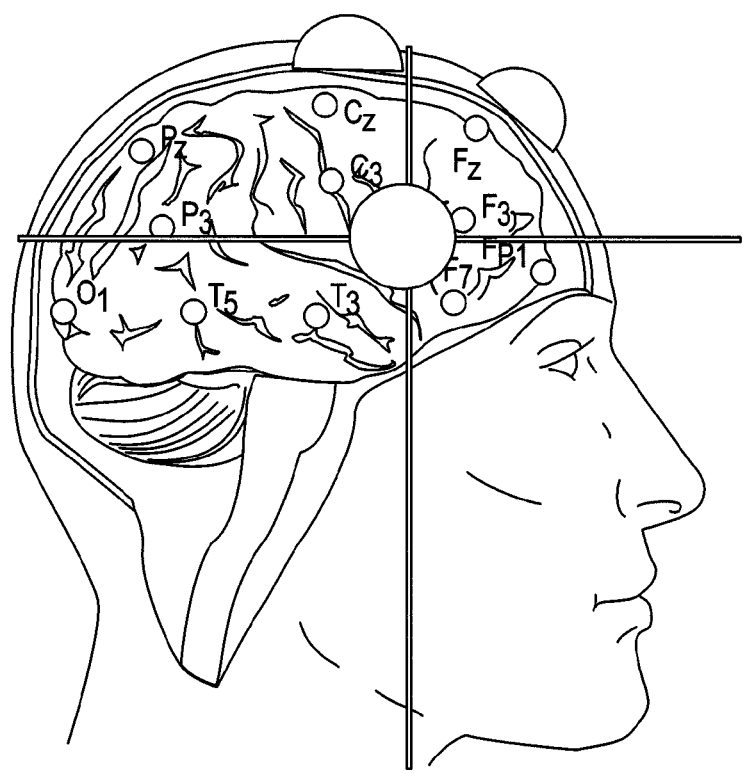

FIGS. 8A-8D illustrate a diamond-shaped configuration of four magnets in which the constituent magnets are placed in the same polarity and essentially the same orientation. For example, FIG. 8A shows one example of a four coil array having four TMS electromagnets (coils 1-4) arranged around the subject's head. FIG. 8A shows a top view and FIG. 8C shows a side perspective view.

Figure 8D:
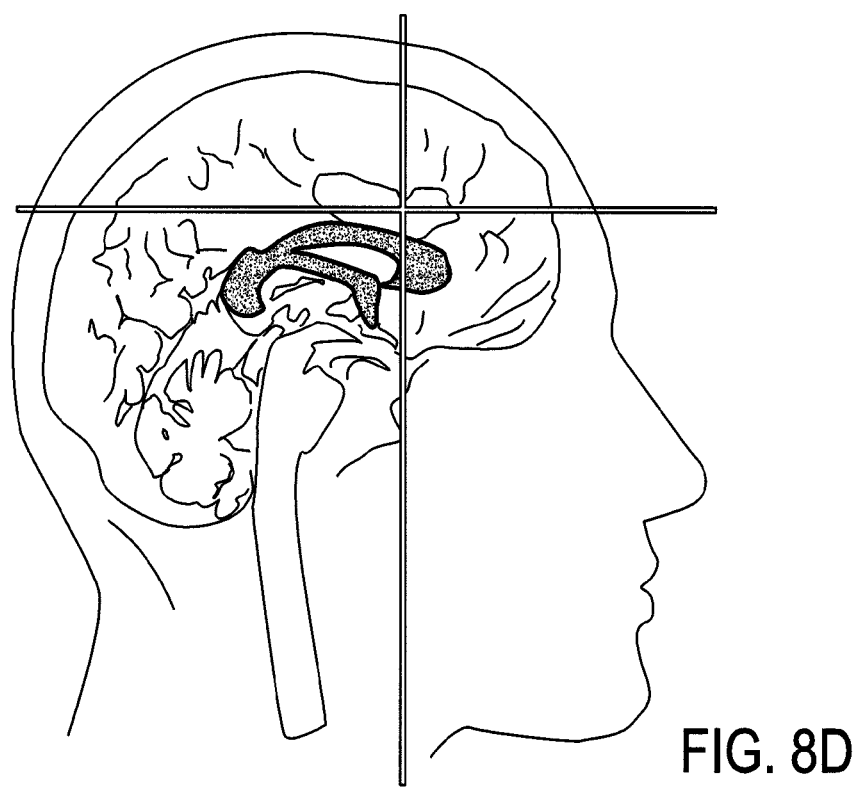

In FIG. 8A-8D, the coils may be arranged so that the primary coil (coil 2) is between the secondary coils (e.g., coils 1, 3 and 4), that are arranged in terms of EEG-25 landmarks and nomenclature. The positions shown in FIGS. 8A-8D for the TMS electromagnet coils may be arranged to simulate a target region as indicated in FIGS. 8B and 8D, in which the cingulate gyms is the target region. Other regions may be targeted by moving or repositioning the array of TMS electromagnets.

Alternatively, the coils shown in FIG. 8A-8D, may be arranged so that there are two primary coils (coils 1 and 2) and two secondary coils (coils 3 and 4), that are arranged in terms of EEG-25 landmarks and nomenclature. The same deep brain region may be targeted as indicated in FIGS. 8B and 8D, in which the cingulate gyms is the target region. Other regions may be targeted by moving or repositioning the four coil ("diamond") array of TMS electromagnets.

In general, any of the arrays and TMS electromagnets described herein may be moved around a subject's head to target one or more regions. For example, the entire array may be moved together to target one or more regions. In some variations, the array is moved to temporally summate stimulation at a single target (e.g., deep brain) site when stimulating from different positions around the subject's head. This may minimize energy applied by the TMS electromagnets at intervening (e.g., more superficial) sites. Examples of this are described in U.S. Pat. No. 7,520,848, previously incorporated by reference in its entirety. In some variations, the arrangement of the TMS electromagnets (spacing and aiming of the TMS electromagnets) within an array may also be adjusted as the array is moved around the subject's head. In particular, the arrangement may be kept substantially the same, but adjusted so that the focusing of the TMS electromagnet is maintained. In any variation, the power applied to the secondary TMS electromagnets may be adjusted relative to the primary TMS electromagnet(s) as the target changes and/or the position of the array moves relative to the subject's head.

Figure 9A:
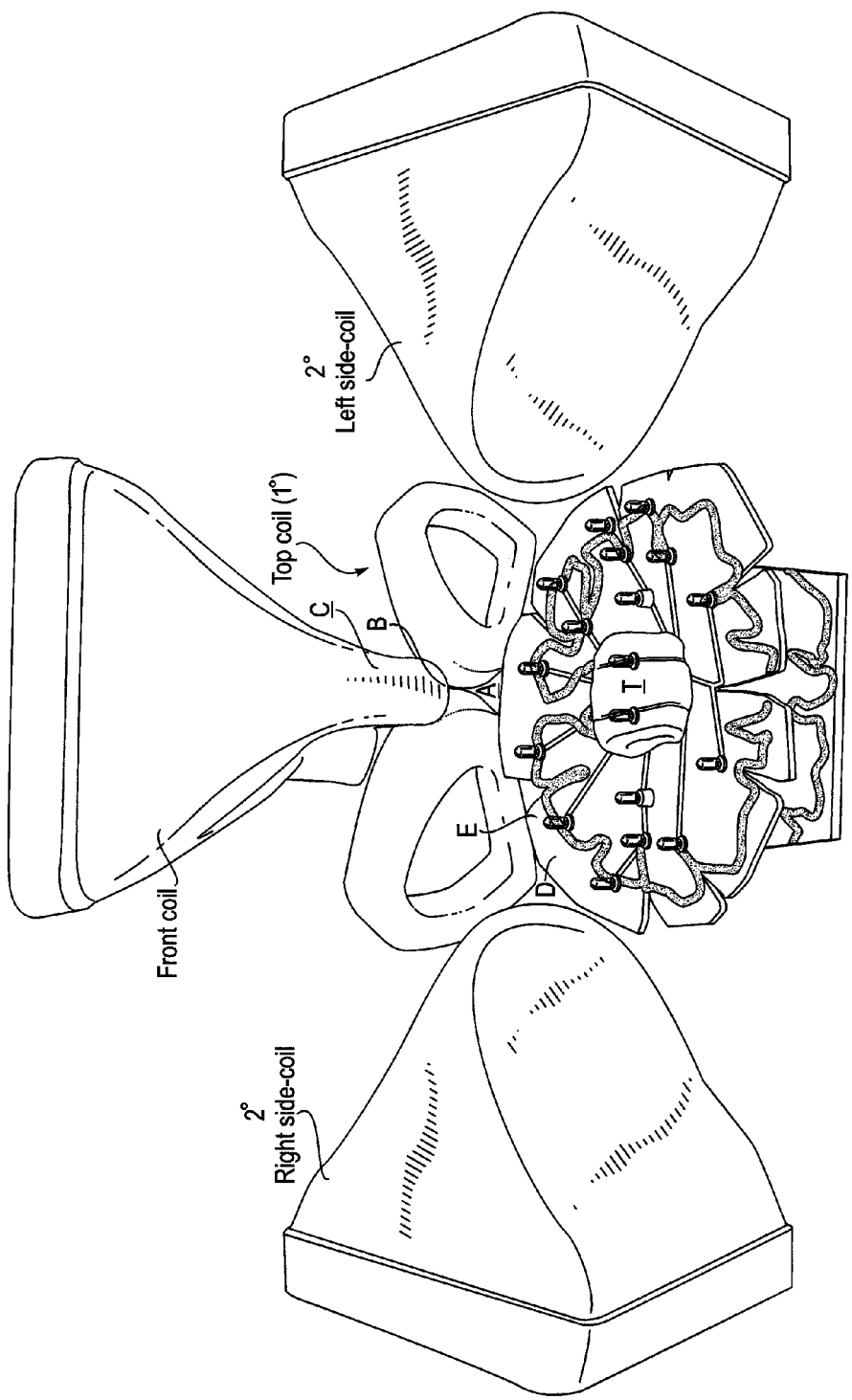
FIGS. 9A-9C illustrate a diamond array as described in FIGS. 8A-8D with a testing 3D phantom that registers the field resulting from the array, and particularly the out-of-plane fourth TMS electromagnet coil.

FIG. 9A shows an exemplary layout of an array of four TMS electromagnets, using prototype coils arranged to the specification of the configuration similar to that defined in FIG. 8A. Specifically, this example includes a (patient's) right-side secondary coil with an I-bottom V design, a left secondary side-coil with an I-bottom V design, a front secondary coil of I-bottom V design and a primary ("center") coil of flat bottomed V or swept-wing V design. Thus, the two side coils and the top/front coil are all secondary TMS electromagnets, while the primary coil is referred to as the "center" coil (between the secondary coils around the "head" of the phantom). Use of flat double coils may also be advantageous in the top and center positions. The phantom shown with the array is based on the proportions of brain and brain tracts in the Talairach Atlas, as described above for FIGS. 6-7F. Simulated tracts are made of 12 turns (each) of #32 lacquer-insulated copper magnet wire, with standard light-emitting diodes directly soldered to the ends of the loops. Arcuate fascicule near the simulated cortex are formed in circular arrangements in loop diameters comparable with those in an actual adult brain. The medial-lateral tracts of the corona radiata are represented at intervals. The superior longitudinal fascicule are simulated with elongated loops extending the length of ⅝" diameter dowels approximately 3 inches in length. In keeping with the anatomy of the cingulate gyrus and tracts, the simulated cingulate nerve bundle is composed of wire loops oriented in the anterior-posterior direction through most of the phantom, but curving in a "J" shape, downward in a simulated cingulate genu. LEDs connected to each simulated tract illuminate in accordance with the amount of electrical current induced in them by the magnet array pulses, and may be recorded for analysis in a photogrammetric fashion. Since each simulated tract has the same number of wire turns, the amount of current induced in each simulated tract reflect the change in magnetic field strength per unit time which courses in the same direction as the copper loops of the simulated tract. Hence the direction of the tracts is a critical factor in determining which will be preferentially stimulated. The individual $B_x$, $B_y$, and $B_z$ components of the magnetic field may be more important than the overall magnetic field, $B=SQRT(B_x^2+B_y^2+B_z^2)$. Using such direction control, induced electrical current in the cingulate bundle can be directed in the anterior to posterior direction to suppress or stimulate cingulate activity.

Figure 9B:
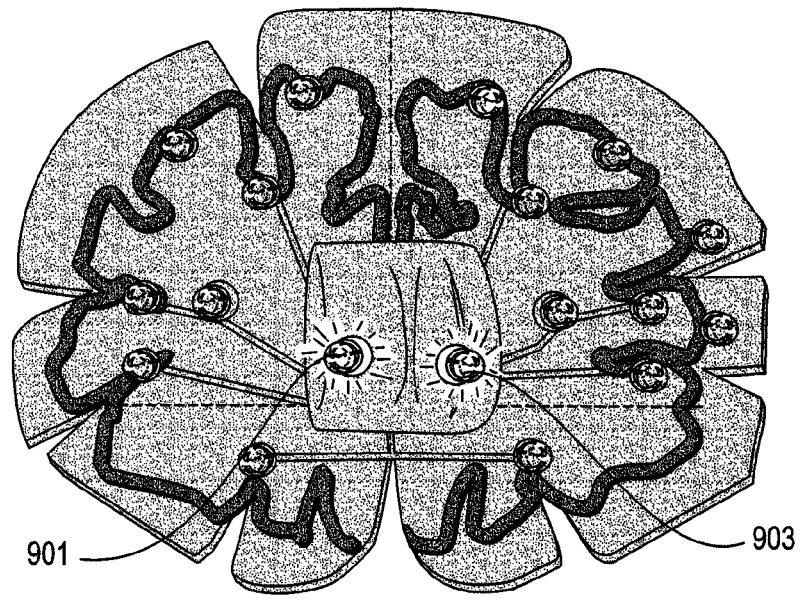

FIG. 9B indicates stimulation of the cingulate bodies using the TMS electromagnet array shown in FIG. 9A, resulting in stimulation of the simulated cingulate bundles in the phantom, without significant applied magnetic field (illumination) of the surrounding simulated tracts. This is apparent by the lighting up of the LEDs representing the cingulate region 901, 903, but not the surrounding LEDs representing adjacent "tracts". In this example, focused deep-brain stimulation occurs when the center coil is powered at 25% power, the left side-coil at 10% power, the right side-coil at 10% power, and the top (central anterior) coil at 25% power. The percentage power may be percentage of MT. These relationships may be scaled linearly, such that an equivalent power used in a human brain might typically be center coil 100% power, the left side-coil at 40% power, the right side-coil at 40% power, and the top (central anterior) coil at 100% power (or less). Even though the total magnetic field strength is greater in the periphery (e.g., non-target regions), near each magnet of the array, the cingulate bundles may effectively act as large antennas which efficiently pick up magnetic field pulses when the array is oriented with respect to the anatomy in the manner shown.

Figure 9C:
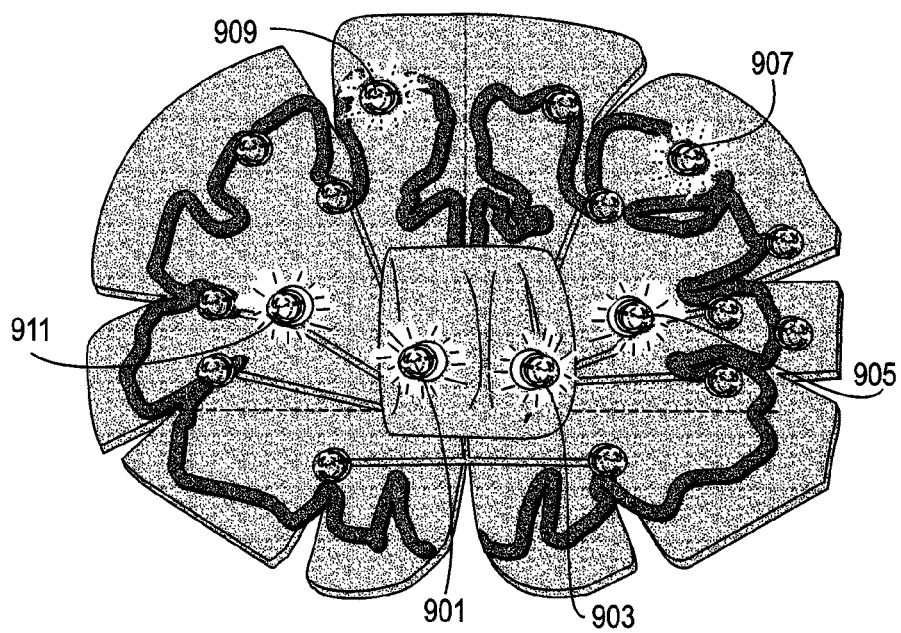

FIG. 9C illustrates the same array in which the TMS electromagnets are poorly balanced by the application of different powers to the coils, resulting in poor focality, illuminating both the central 901, 903 LEDs and off-center LEDs 905, 907, 909, 911. Note that the coils here are powered so that the center coil has 80% power, the left side-coil at 60% power, the right side-coil at 60% power, and the top (central anterior) coil at 80% power. However, if the illuminated regions did represent a host of brain areas that one wished to stimulate for example, for the treatment of a specific disease, this set of power ratios might be appropriate. Thus, it may be appreciated that the magnetic field and induced electrical current may be shaped in the context of the magnet array shape, the power ratio of the coils, and the specific conductivity and geometry of the anatomy. The secondary coils in the example shown in FIGS. 9A-9C (e.g., the side coils) are stimulated with the same polarity as the primary coils. As mentioned above, greater focality has been observed when stimulating with opposite polarity.

Note that power settings may be unique to a given coil design, such that say, 40% power of one magnet type might be equivalent to 50% power of another magnet design. The ratio of power applied (e.g., higher percentages applied to the primary TMS electromagnets compared to the secondary TMS electromagnets) maybe constant, and the applied power may be scaled appropriately (e.g., to determine MT). In some variations, the power is referred to with reference to the primary TMS electromagnet in the array. For example, the primary TMS electromagnet may be stimulated with a power chosen as a percentage of MT (e.g., 80% MT, 90% MT, etc.) while the secondary TMS electromagnets may be stimulated as a percentage of the power of the primary TMS electromagnet (e.g., 90%, 80%, 70%, 60%, etc., of the power of the primary TMS electromagnet). In some variation, feedback of the field strength of the resulting magnetic field emitted by each TMS electromagnet may be used to calibrate the power of each TMS electromagnet.

Whether the current applied to the secondary TMS electromagnets is the same or opposite polarity to that of the main coil(s), the magnetic field may be shaped to induce current in the target as desired. In some variations, the application of current to the array, and particularly to the secondary TMS electromagnets, can be chosen so that the induced current in the target is induced in a desired direction or orientation. For example, induced electrical current in the cingulate bundle can be directed in the anterior to posterior direction to suppress or stimulate cingulate activity depending on the firing frequency. Typically, suppression are believed to occur with electromagnet firing rates of 1 Hz or less and stimulation at rates above 1 Hz. In the case of the surrounding (secondary) magnets being fired with opposite polarity from the primary magnet, the directionality of the induced electrical field occurs with increased focus, but at a lower magnitude.

The table shown in FIG. 10 illustrates an in vivo example of an array of TMS electromagnets such as that shown in FIG. 9A, including a primary TMS electromagnet in the center position, and three secondary TMS electromagnets, two placed laterally (at approximately 90 degrees to the primary coil) and one in front. This array was arranged around the test subjects so that the primary TMS electromagnet was placed near the top of the subject's head and the secondary TMS electromagnets were placed laterally and near the front (e.g., forehead/eyes) of the subject.

In FIG. 10, TMS was performed on each of the test subjects targeting the prefrontal cingulate a response to a painful stimuli was given. Brain activity was observed by imaging. For example, in subjects 1-10, the primary coil and the secondary coils were stimulated with opposite polarity at the various powers indicated in column 4 ("Highest coil percentage powers used"). The primary TMS electromagnet corresponds to the "top", while the secondary coils include the "left/right/front" as indicated. Focusing of the resultant magnetic field is inferred from the specificity of inhibition or suppression of activity in the cingulate, as well as analgesia. In four of the cases (subjects 1, 2, 3, and 8), successful field shaping is inferred by the preferred cinguate suppression and analgesia observed. In these patients, the primary TMS electromagnet was stimulated near above the MT while the secondary TMS electromagnets (and particularly the lateral left/right TMS electromagnets) were energized to much less than the primary TMS electromagnet. A similar, though less dramatic, effect was seen in subjects 6, 7, and 9. In contrast, when the secondary TMS electromagnets, and particularly the lateral (left/right) TMS electromagnets were stimulated at the same or nearly the same level as the primary TMS electromagnet (as in subject's 4, 5, and 10), the cingulate was not preferentially targeted (meaning adjacent structures were also targeted), and/or the cingulate was not suppressed. In some cases (e.g., subject 5 and 10), the patient actually demonstrated up-regulation of the cingulate and hyperalgesia. Curiously, when the polarity of the primary and secondary coils was the same, hyperalgesia resulted, as seen in subject's 14 and 15.

In FIG. 10, the percentage of motor threshold (% MT) is determined as the percentage of the power driving the top coil (e.g., available power from the power supply driving the top coil). Similarly, the highest coil percentage powers used (for the top/left/right/front) refers to the percentage of power available by the (identical) power supplies feeding each of the top, left, right and front TMS electromagnets. These percentages may be normalized by the % MT for cross-comparison.

This preliminary study suggests that the in vivo effect of TMS filed shaping is consistent with that seen using the phantom testing. In particular, it may be beneficial to energize the secondary coils at an opposite-polarity and a lower stimulation level than the primary coil when shaping the field of the primary coil to achieve deep brain stimulation.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

What is claimed is:

1. A Transcranial Magnetic Stimulation (TMS) system for stimulating a subject's neuronal tissue configured for shaping an emitted magnetic field to modulate a brain target, the system including:
   a primary TMS electromagnet configured to apply TMS to the subject; and
   one or more secondary TMS electromagnets, configured to be activated concurrently with the primary TMS electromagnet to apply TMS to the subject and to shape a magnetic field emitted by the primary TMS electromagnet, wherein the one or more secondary TMS electromagnets are configured to emit a magnetic field that is concurrent with and shapes the magnetic field emitted by the primary TMS electromagnet; and
   one or more power sources comprising an oscillator for delivering a pulsed power to the primary TMS electromagnet and one or more secondary TMS electromagnets.

2. The system of claim 1, further wherein the one or more secondary TMS electromagnets comprises at least two secondary TMS electromagnets, wherein the primary and one or more secondary TMS electromagnets are configured so that the primary TMS electromagnet may be positioned between the at least two secondary TMS electromagnets around the subject's head.

3. The system of claim 1, wherein the one or more secondary TMS electromagnets are configured to stimulate in a same polarity as the primary TMS electromagnet.

4. The system of claim 1, wherein the one or more secondary TMS electromagnets are configured to stimulate in an opposite polarity as the primary TMS electromagnet.

5. The system of claim 1, further comprising additional primary TMS electromagnets.

6. The system of claim 1, wherein the primary TMS electromagnet and the one or more secondary TMS electromagnets are two-coil TMS electromagnets having different geometries.

7. The system of claim 1, wherein the primary TMS electromagnet is a flat-bottomed TMS electromagnet and the one or more secondary TMS electromagnets are V-shaped TMS electromagnets.

8. The system of claim 1, further comprising a controller configured to coordinate an application of power to the primary and one or more secondary TMS electromagnets.

9. The system of claim 1, further comprising a frame configured to secure the primary and one or more secondary TMS electromagnets so that the primary TMS electromagnet may be positioned between two secondary TMS electromagnets of the one or more secondary TMS electromagnets around a subject's head.

10. The system of claim 1 comprising three secondary TMS electromagnets.

11. The system of claim 1, wherein the primary TMS electromagnet is configured to focus on a brain target and the one or more secondary TMS electromagnets are configured to have a different focus from the focus of the primary TMS electromagnet.

12. A Transcranial Magnetic Stimulation (TMS) system for stimulating a subject's neuronal tissue, the system including:
   a primary TMS electromagnet configured to apply Transcranial Magnetic Stimulation to the subject; and
   at least one secondary TMS electromagnet configured to shape a magnetic field emitted by the primary TMS electromagnet, and wherein the at least one secondary TMS electromagnet is configured to be activated when the primary TMS electromagnet is activated and to emit a magnetic field that is of opposite polarity and is concurrent with and shapes the magnetic field emitted by the primary TMS electromagnet; and
   one or more power sources comprising an oscillator for delivering a pulsed power to the primary TMS electromagnet and the secondary TMS electromagnet.

13. A Transcranial Magnetic Stimulation (TMS) system for stimulating a subject's neuronal tissue, the system including:
   a primary TMS electromagnet configured to apply Transcranial Magnetic Stimulation to the subject;
   a plurality of secondary TMS electromagnets configured to shape a magnetic field emitted by the primary TMS electromagnet, wherein the secondary TMS electromagnets are configured to be activated concurrently with activation of the primary TMS electromagnet and to emit a magnetic field that is opposite in polarity and concurrent with the magnetic field emitted by the primary TMS electromagnet; and
   one or more power sources comprising an oscillator for delivering a pulsed power to the primary TMS electromagnet and the secondary TMS electromagnets, and
   wherein the primary TMS electromagnet is configured to be positioned between the secondary TMS electromagnets around the patient's head.

14. The system of claim 13, wherein the primary TMS electromagnet and the secondary TMS electromagnets are two-coil TMS electromagnets having different geometries.

15. The system of claim 13, wherein the primary TMS electromagnet is a flat-bottomed TMS electromagnet and the secondary TMS electromagnets comprise V-shaped TMS electromagnets.

16. The system of claim 13, further comprising a controller configured to coordinate an application of power to the primary and secondary TMS electromagnets.

17. The system of claim 13, further comprising a frame configured to secure the primary and secondary TMS electromagnets so that the primary TMS electromagnet is positionable between the secondary TMS electromagnets around a patient's head.

18. The system of claim 13 comprising three secondary TMS electromagnets.

19. A method of performing Transcranial Magnetic Stimulation (TMS) of target deep brain structures by shaping a magnetic field emitted by a primary TMS electromagnet, the method comprising:
   positioning a primary TMS electromagnet between a plurality of secondary TMS electromagnets around a subject's head; and
   shaping the magnetic field emitted by the primary TMS electromagnet to modulate a deep brain target by simultaneously emitting a magnetic field from the primary TMS electromagnet and each of the plurality of secondary TMS electromagnets, modulating the deep brain target; and
   one or more power sources comprising an oscillator for delivering a pulsed power to the primary TMS electromagnet and the secondary TMS electromagnets.

20. The method of claim 19, wherein the magnetic field emitted by the secondary TMS electromagnets has an opposite polarity of the primary TMS electromagnet.

21. The method of claim 19, further comprising aiming the primary TMS electromagnet at the deep brain target within the subject's brain.

\* \* \* \* \*